US007829348B2

(12) United States Patent
Porter et al.

(10) Patent No.: US 7,829,348 B2
(45) Date of Patent: Nov. 9, 2010

(54) RAMAN-ACTIVE REAGENTS AND THE USE THEREOF

(75) Inventors: Marc D. Porter, Ames, IA (US); Jing Ni, San Jose, CA (US); Robert J. Lipert, Ames, IA (US); G. Brent Dawson, San Jose, CA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 369 days.

(21) Appl. No.: 10/931,142

(22) Filed: Aug. 31, 2004

(65) Prior Publication Data

US 2005/0089901 A1 Apr. 28, 2005

Related U.S. Application Data

(63) Continuation-in-part of application No. 09/961,628, filed on Sep. 24, 2001.

(60) Provisional application No. 60/234,608, filed on Sep. 22, 2000.

(51) Int. Cl.
*G01N 33/553* (2006.01)
(52) U.S. Cl. .................. 436/525; 436/164; 436/514
(58) Field of Classification Search ................ 436/525, 436/164, 514, 166, 172, 518, 540, 541, 523, 436/524, 536, 539, 805; 356/301, 317, 318, 356/337; 435/7.92, 7.93, 7.94, 7.95, 968, 435/973, 975
See application file for complete search history.

(56) References Cited

U.S. PATENT DOCUMENTS

| 5,252,459 | A | * | 10/1993 | Tarcha et al. | ................ | 435/6 |
|---|---|---|---|---|---|---|
| 5,266,498 | A | | 11/1993 | Tarcha et al. | | |
| 5,380,833 | A | * | 1/1995 | Urdea | .................. | 536/22.1 |
| 5,445,972 | A | | 8/1995 | Tarcha et al. | | |
| 5,567,628 | A | | 10/1996 | Tarcha et al. | | |
| 5,817,795 | A | | 10/1998 | Gryaznov et al. | | |
| 6,319,670 | B1 | * | 11/2001 | Sigal et al. | .................. | 435/6 |
| 6,770,488 | B1 | * | 8/2004 | Carron et al. | ............... | 436/525 |

FOREIGN PATENT DOCUMENTS

WO WO99/44065 9/1999

OTHER PUBLICATIONS

Dou, X., et al., "Enzyme Immunoassay Utilizing Surface-Enhanced Raman Scattering of the Enzyme Reaction Product," Anal. Chem. 69:1492-1495 (1997).

(Continued)

*Primary Examiner*—Jacob Cheu
*Assistant Examiner*—Pensee T Do
(74) *Attorney, Agent, or Firm*—McKee, Voorhees & Sease, P.L.C.

(57) ABSTRACT

The present invention provides a new class of Raman-active reagents for use in biological and other applications, as well as methods and kits for their use and manufacture. Each reagent includes a Raman-active reporter molecule, a binding molecule, and a surface enhancing particle capable of causing surface enhanced Raman scattering (SERS). The Raman-active reporter molecule and the binding molecule are affixed to the particle to give both a strong SERS signal and to provide biological functionality, i.e. antigen or drug recognition. The Raman-active reagents can function as an alternative to fluorescence-labeled reagents, with advantages in detection including signal stability, sensitivity, and the ability to simultaneously detect several biological materials. The Raman-active reagents also have a wide range of applications, especially in clinical fields (e.g., immunoassays, imaging, and drug screening).

23 Claims, 13 Drawing Sheets

(a) Co-immobilization approach (b) Covalent linking approach

OTHER PUBLICATIONS

Martin, C.R., et al., "Nanomaterials in Analytical Chemistry," Analytical Chemistry News & Features, 322-327 (May 1998).

Nie, S. et al., "Probing Single Molecules and Single Nanoparticles by Surface-Enhanced Raman Scattering," Science 275:1102-1106 (1997).

Rohr, T.E., et al., "Immunoassay Employing Surface-Enhanced Raman Spectroscopy," Anal. Biochem. 182:388-398 (1989).

Wagner, P., et al., "Covalent Immobilization of Native Biomolcules onto Au(111) via N-Hydroxysuccinimide Ester Functionalized Self-Assembled Monolayers . . . ," Biophys. J. 70:2052-2066 (1996).

* cited by examiner (1) Creation of capture antibody surface (2) Exposure to analyte (3) Development with reporter labeled immunogold Antibodies Antigens Reporters A  Original SERS reagent synthesis B  Refined SERS reagent synthesis Antibody        30 nm Gold Particle Reporter        Reporter with reactive group R

RAMAN-ACTIVE REAGENTS AND THE USE THEREOF

CROSS-REFERENCE TO RELATED APPLICATIONS

This application is a continuation-in-part of application Ser. No. 09/961,628, filed Sep. 24, 2001, which claims the benefit of U.S. Provisional Application 60/234,608, filed Sep. 22, 2000.

STATEMENT REGARDING FEDERALLY SPONSORED RESEARCH OR DEVELOPMENT

None.

BACKGROUND OF THE INVENTION

Many assays exist for detecting and measuring analytes of small quantity in the presence of a large volume of other substances. Such assays typically make use of the high binding affinity between the analyte (the substance to be detected or measured) and a second molecule having a high degree of specificity for binding to that analyte. These assays are often referred to as ligand-binding assays.

One of the most common ligand-binding assays are immunoassays. Immunoassays typically employ an antigen and an antibody which specifically binds to the antigen to form an antibody/antigen complex. In order to measure the extent of the antibody/antigen binding, one member of the complex is generally labeled or tagged with a traceable substance. The presence of the traceable substance, and hence the presence of the antibody or antigen to which it is attached, may then be detected or measured using a variety of different techniques depending upon the unique characteristics of the label employed. These techniques may include scintillation counting, fluorescence, absorption, electrochemistry, chemiluminescence, Rayleigh scattering and Raman scattering. Of these techniques, fluorescence spectroscopy has been one of the most widely used readout methods, primarily because of its high sensitivity.

Although fluorescence spectroscopy has seen substantial use in scientific research and clinical diagnostics, there are disadvantages in using fluorescence spectroscopy. For instance, the different types of fluorescent molecules used in fluorescence spectroscopy typically require excitation with photons of differing wavelengths. Therefore, if the detection of multiple fluorescent molecules is desired in a single sample, multiple light sources may be required. Even so, the spectral overlap between the emission of the different fluorescent molecules often limits reliable individual and quantitative detection of multiple analytes in a single sample.

Today, many assays require the concomitant determination of more than one analyte in a single test sample (e.g., the screening of cancer markers, such as α-fetoprotein and carcinoembryonic antigen). There are two general approaches to assaying multiple analytes in a single sample. One approach immobilizes different binding molecules on a solid support at spatially separated addresses. Multiple analytes can then be detected using the same label, with identification based on address location. Alternatively, different labels can be used to detect multiple analytes simultaneously in the same spatial area. In this case, each analyte obtains its own distinct label.

We have explored Raman spectroscopy as an alternative to fluorescence spectroscopy. Raman spectroscopy measures the level of Raman scattering induced by the application of a radiation source, i.e. light source, on an analyte. The light incident on the analyte is scattered due to excitation of electrons in the analyte. "Raman" scattering occurs when the excited electron returns to an energy level other than that from which it came, resulting in a change in the wavelength of the scattered light and giving rise to a series of spectral lines at both higher and lower frequencies than that of the incident light. The series of spectral lines is generally called the Raman spectrum.

Conventional Raman spectroscopy usually lacks sufficient sensitivity for use as a readout method for immunoassays. Raman spectroscopy is also unsuccessful for fluorescent materials because the broad fluorescence emission bands tend to swamp the weaker Raman bands.

However, a modified form of Raman spectroscopy based on "surface enhanced" Raman scattering (SERS) has proved to be more sensitive and thus of more general use. In the SERS form of Raman spectroscopy, the analyte whose spectrum is being recorded is closely associated with a roughened metal surface. This close association leads to a large increase in detection sensitivity, the effect being greater the closer the proximity of the analyte to the metal surface.

The manner in which surface enhancement occurs is not yet fully understood, but it is thought that the incident light excites conduction electrons in roughened metal surfaces or particles, generating an electron plasma resonance (plasmon). As a result, the electromagnetic field in the vicinity of the metal surface is greatly amplified, giving rise to enhanced Raman scattering for molecules located close to the surface.

Surprisingly, there have been only a few reports on the application of SERS for detection in immunoassays. Two of these approaches used a sandwich-type assay, which coupled surface and resonance enhancements. In particular, Rohr et al., *Anal. Biochem.* 1989, 182, 388, used labeled detection antibodies and roughened silver films coated with a capture antibody (see also U.S. Pat. No. 5,266,498 to Tarch et al.), and Dou et al., *Anal. Chem.* 1997, 69, 1492, exploited the adsorption on silver colloids of an enymatically amplified product. Another approach by White et al., International Application Publication No. WO 99/44065, employs an immunoassay based on the displacement of SERS and surface enhanced resonance Raman (SERRS) active analyte analogs which are modified so as to have particular SERS and SERRS surface seeking properties. Upon introduction of a sample, the analyte analogs are displaced by the analyte of interest in the sample and exposed to a SERS or SERRS surface, such as an etched or roughened surface, a metal sol or an aggregatation of metal colloid particles. Raman spectroscopy is then performed to detect the displaced analyte analog associated with the SERS or SERRS surface to determine the presence or quantity of the analyte in the sample.

A major barrier that prohibits using SERS for the direct detection of biological samples is that the surface enhancement effect diminishes rapidly with increasing distance from the metallic surfaces. In other words, strong SERS signals are observed only if the scattering centers are brought into close proximity (<100 nm) to the surface. In addition, although Raman spectra of biomolecules can be obtained on silver surfaces when coupling SERS and resonance enhanced scattering, the spectra are usually lacking of sufficient chemical content and/or signal amplitude to be used for immunoassay purposes.

We have overcome these barriers by developing a novel class of Raman-active reagents having both Raman-active reporter molecules and binding molecules integrated with each other on the same SERS surface. In each of the above systems, the SERS or SERRS surface and the Raman-active molecule are not integrated with each other, but are merely placed in close proximity to each other by the combination of an analyte sandwiched between an antibody immobilized on the enhancing surface and an antibody attached to a Raman-active molecule, or the combination of the SERS or SERRS surface with a particular SERS or SERRS surface seeking group coupled to an analyte analog and a Raman-active molecule, after exposure to the sample.

BRIEF SUMMARY OF THE INVENTION

The present invention is summarized as a novel class of Raman-active reagents for use in biological and other applications, as well as methods and kits for their use and manufacture.

The Raman-active reagents each include a Raman-active reporter molecule, a binding molecule, and a surface enhancing particle capable of causing surface enhanced Raman scattering. The Raman-active reporter molecule and the binding molecule are operably linked to the particle to give both a strong surface enhanced Raman scattering (SERS) signal and to provide biological functionality, e.g. antigen or drug recognition. The Raman-active reporter molecule and the binding molecule may be either directly linked to the surface enhancing particle or indirectly linked to the surface enhancing particle by way of a linker molecule. In one embodiment, the Raman-active reporter molecule and the binding molecule are each independently linked to the surface enhancing particle. In a second embodiment, the binding molecule is operably linked to the Raman-active reporter molecule, which is operably linked to the surface enhancing particle. Other variations are possible.

The Raman-active reagents may be employed to determine the presence or amount of a target analyte in a test sample by use of the binding specificity of the binding molecule for the target analyte, or a portion thereof, and the generation and measurement of SERS signal induced by the application of a radiation onto the reagent/analyte complex. The Raman-active reagents may be used, for example, in clinical, forensic, and water quality testing labs for the detection of drugs, pesticides, bacteria, viruses, microbial toxins, hormones and biologically important proteins, industrial chemicals, explosives, trace metals, etc.

The Raman-active reagents may be manufactured in the lab or provided to the user in the form of a kit. The kit may include a previously prepared Raman-active reagent, or the ingredients for manufacturing the Raman-active reagents in the lab. The kit may also include ingredients that minimize nonspecific binding and ingredients that stabilize the reagent to extend its shelf life. In addition, the kit may include a capture substrate covered with binding molecules to immobilize analytes for subsequent detection with the Raman-active reagent. For the simultaneous detection of multiple analytes, the kit may also include unreactive spacer molecules, such as molecules terminated with ethylene glycol units, for interspersing amongst the binding molecules so as to minimize steric interferences as well as to resist nonspecific adsorption.

In one embodiment, the Raman-active reagents are manufactured by coimmobilizing the Raman-active reporter molecules and the binding molecules to metal colloid particles. In the case of gold particles, the reporter molecules can be covalently linked to the particle through thiol functionalities on the reporter molecules. Binding molecules, for example, antibodies, will spontaneously associate with unreacted areas of the particle to form a Raman-active reagent for antigen detection. In a second embodiment, the Raman-active reagents are manufactured by covalently linking the Raman-active reporter molecules to the surface enhancing particle, and by covalently linking the binding molecules to the Raman-active reporter molecules.

It is one object of the present invention to provide a new class of labeling reagents as an alternative to fluorescence-labeled reagents. It is also an object of the present invention to provide a new class of labeling reagents capable of simultaneously detecting multiple analytes in a single test sample.

The Raman-active reagents of the present invention serve as an alternative to fluorescence-labeled reagents, with advantages in detection including signal stability, sensitivity, and the ability to simultaneously detect several analytes in a single test sample. Because of the ability to simultaneously detect several analytes in a single test sample, faster analysis speeds and reduced labor costs may be obtained.

In yet another embodiment, the invention provides a novel reagent for low-level detection in immunoadsorbent assays. The reagent consists of gold nanoparticles modified with succinimide ester derivatives such as, for example 5,5'-dithiobis (succinimidyl-2 nitrobenzoate) to integrate bioselective species (e.g., antibodies) with molecular labels to generate SERS responses. The reagent is constructed by coating gold nanoparticles (30 nm) with a monolayer of an intrinsically strong Raman scatterer. These monolayer-level labels are bifunctional by design and contain disulfides for chemisorption to the nanoparticle surface and succinimides (i.e., reactive group) for coupling to the bioselective species.

An object of this embodiment is to provide a label design that both minimizes the separation between label and particle surface and maximizes the number of labels on each particle.

Another object of this embodiment is to provide a novel approach to SERS-based labeling with the following advantages: narrow spectral bandwidth, resistance to photobleaching and quenching, and long-wavelength excitation of multiple labels with a single excitation source.

Yet another aspect of this embodiment is that it enables the detection of antigens, for example, free prostate-specific antigen (PSA) using a sandwich assay format based on monoclonal antibodies.

In still another aspect, this embodiment provides detection limits of approximately 1 pg/mL in human serum and approximately 4 pg/mL in bovine serum albumin at a spectrometer readout time of 60 s.

In another aspect, this embodiment may be used in conjunction with multianalyte assays to simultaneously determine many complexed forms of antigens, such as for example, PSA.

Other objects, features and advantages of the present invention will be apparent in the following Detailed Description of the Invention when read in conjunction with the accompanying drawings, examples and claims.

DETAILED DESCRIPTION OF THE INVENTION

Figure 1:
FIG. 1 illustrates two possible methods for preparing Raman-active immunogold reagents.
Figure 1:
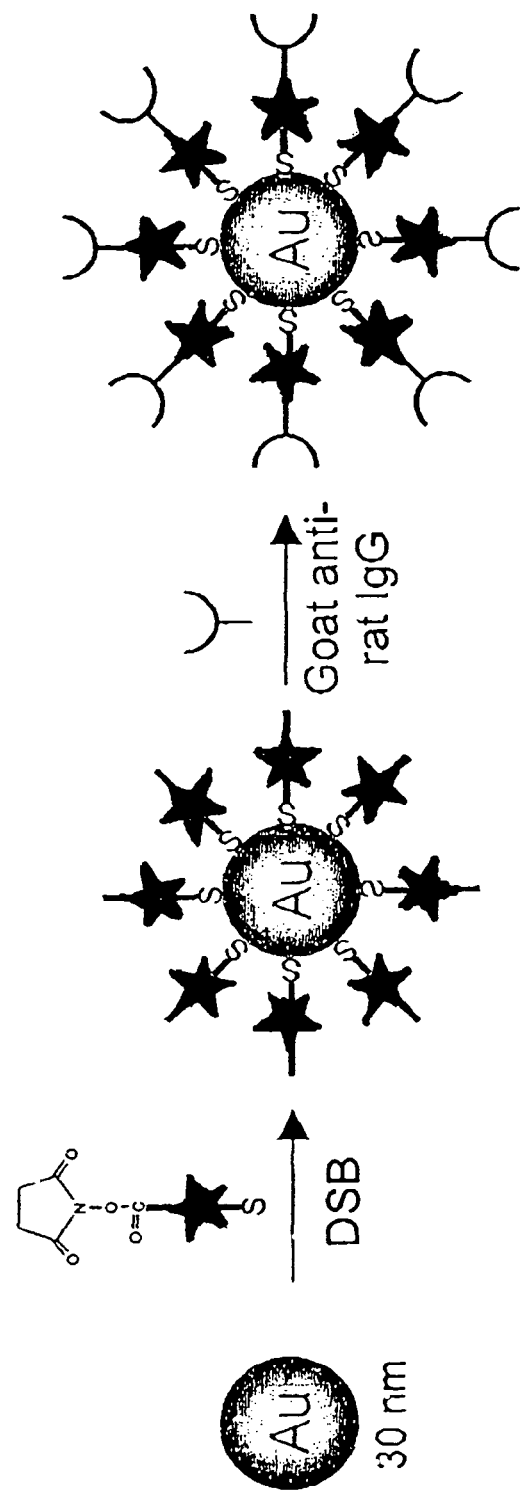

The present invention provides a novel class of Raman-active reagents for use in determining the presence or amount of a target analyte in a test sample. Also provided are particular methods and kits for using the Raman-active reagents of the present invention, as well as certain novel, preferred, methods for their manufacture.

The Raman-active reagents according to the present invention comprise a Raman-active reporter molecule, a binding molecule, and a surface enhancing particle capable of causing surface enhanced Raman scattering. The Raman-active reporter molecule and the biological binder are operably linked, either directly or indirectly, to the surface enhancing particle to give both a strong surface enhanced Raman scattering (SERS) signal and specific binding affinity to a target analyte. The Raman-active reporter molecule and the binding molecule may be either directly linked to the surface enhancing particle or indirectly linked to the surface enhancing particle by way of a linker molecule. The Raman-active reporter molecule and the binding molecule may be independently linked to the surface enhancing particle, or the binding molecule may be operably linked to the Raman-active reporter molecule, which is operably linked to the surface enhancing particle.

The term "surface enhancing particle" is defined herein to include particles capable of causing surface enhanced Raman scattering. Particles capable of causing surface enhanced Raman scattering are well known in the art and generally include, without limitation, particles of metallic materials such as gold, silver, copper, platinum, aluminum, gallium, indium, zinc, cadmium, lithium and sodium. The particles may also include, without limitation, other inert support structures of silica, plastic, glass, carbon, ceramics, or other materials, including magnetic materials, coated with a metallic material capable of causing surface enhanced Raman scattering, such as the metallic materials listed above.

The particles used in the present invention are colloid particles. The colloid particles are preferably of a uniform and desired size and shape and stabilized against possible self-aggregation. Processes for preparing unaggregated colloids are well known in the art and typically involve, for example, the reduction of a metal salt (e.g., silver nitrate) with a reducing agent (e.g., citrate) to form a stable microcrystalline suspension. Stabilization may also be realized by the use of thin films or monolayers of various organic compounds. The colloid particles can be of any size as long as they give rise to an SERS signal. For example, the colloid particles may be less than 1000 nm in diameter, and preferably less than 100 nm in diameter.

In the preferred embodiment, the surface enhancing particles are metallic nanoparticles. The large surface enhancement observed on metallic nanoparticles results in SERS intensities that can be comparable to or even exceeding those for fluorescence. Such a level of enhancement, which may lead to a high detection sensitivity, together with the ease of handling, make metallic nanoparticles more promising than most other types of SERS substrates for use in ligand-binding assay applications. However, nonmetallic particles encapsulated with an enhancing material may also be of value in some applications. Of the various metallic nanoparticles, gold colloids is preferred over silver colloids, despite the fact that silver colloids provide larger enhancements than gold. This is because the greatest Raman enhancements with gold particles are produced with longer wavelength excitation light. This makes it possible to minimize the generation of sample fluorescence, which may interfere with the measurement of the Raman scattering.

The term "Raman-active reporter molecule" is defined to include any one of a large number of molecules with distinctive Raman scattering patterns. Various molecules with distinctive Raman scattering patterns are well known in the art. Examples of such molecules include, but is not limited to, dithiobisbenzonic acid (DBA), 4-mercaptobenzoic acid (MBA), 2-naphthalenethiol (NT), thiophenol (TP), direct red 81, Chicago sky blue, 4,4'-dithiobis(succinimidylbenzoate) (DSB), p-dimethylaminoazobenzene, 1,5-difluoro-2,4-dinitrobenzene, 4-(4-aminophenylazo)phenylarsonic acid monosodium salt, arsenazo I, basic fuchsin, disperse orange 3, HABA (2-(4-hydroxyphenylazo)-benzoic acid, erythrosine B, trypan blue, ponceau S, ponceau SS, 5,5'-dithiobis(2-nitrobenzoic acid), metal complexes and polymeric particles.

For example, in a preferred embodiment of the invention the reporter molecule 5,5'-dithiobis(2-nitrobenzoic acid) may be converted to a corresponding succinimide ester derivative by treatment with the reactive compound, N-hydroxy succinimide (NHS), resulting in formation of 5,5'-dithiobis (succinimidyl-2-nitrobenzoate (DSNB). DSNB can then be coupled to the primary amine group of a tracer antibody through formation of an amide linkage.

The term "reactive compound" is defined to include any molecule having a reactive group including but not limited to succinimides, maleimides, isothiocyanates, isocyanates, acyl azides, sulfonyl chlorides, aldehydes, glyoxals, epoxides, oxiranes carbodiimides, carbonates, arylating agents, acryloyl derivatives, diazoalkanes, diazoacetyl compounds, anhydrides, aziridines, imidoesters, carbonyldiimidazole, or other groups that may be amine reactive, thiol reactive, or nucleophile reactive, such as for example, N-hydroxysuccinimide.

The term "binding molecule" is defined to include any molecule having a binding specificity and avidity for a molecular component of a target analyte, or which is associated with a target analyte. In general, binding molecules are known to those skilled in the art and typically include, without limitation, lectins (including fragments or derivatives thereof which retain binding function), monoclonal and polyclonal antibodies (including immunoreactive fragments or derivatives derived therefrom, which fragments retain all or a portion of the binding function of the antibody), peptides, haptens, aptamers, and nucleic acid molecules (including single stranded RNA, single-stranded DNA, or single-stranded nucleic acid hybrids), and any fragments and derivatives thereof. Crown ethers, cyclodextrins, cryptands, calixarenes, and many other types of ligands could also be used.

The term "target analyte" is defined to include a molecule of an organic or inorganic nature, the presence and/or quantity of which is being tested for, which contains a molecular component (e.g., ligand or sequence or epitope or domain or portion or chemical group or reactive functionality or determinant) for which a binding molecule has binding specificity. The molecule may include, but is not limited to, a nucleic acid molecule, protein, glycoprotein, eukaryotic cell, prokaryotic cell, lipoprotein, peptide, carbohydrate, lipid, phospholipid, aminoglycans, chemical messenger, biological receptor, structural component, metabolic product, enzyme, antigen, antibody, drug, therapeutic, toxin, inorganic chemical, organic chemical, a substrate and the like.

The term "test sample" means a sample to be tested for the presence or amount of a target analyte. The sample may include a target analyte or be free from the presence of the target analyte.

The term "operably linked" is defined to mean a linkage between two different molecules, or a molecule and a particle, of sufficient stability for the purposes of signal enhancement and detection according to the present invention. As known to those skilled in the art, and as will be more apparent by the following embodiments, there are several methods and compositions in which two or more molecules, or a molecule and a particle, may be operably linked utilizing reactive functionalities. Reactive functionalities include, but are not limited to, bifunctional reagents, linker molecules, biotin, avidin, free chemical groups (e.g., thiol, or carboxyl, hydroxyl, amino, amine, sulfo, phosphine, selenide, etc.), and reactive chemical groups (reactive with free chemical groups).

The term "linker" is defined to refer to a compound or moiety that acts as a molecular bridge to operably link two different molecules, or a molecule and a particle, wherein one portion of the linker is operably linked to a first molecule, and wherein another portion of the linker is operably linked to a second molecule or particle. The two different molecules, or the molecule and particle, may be linked to the linker in a step-wise manner. There is no particular size or content limitations for the linker so long as it can fulfill its purpose as a molecular bridge. Linkers are known to those skilled in the art to include, but are not limited to, chemical chains, chemical compounds, carbohydrate chains, peptides, haptens, and the like. The linkers may include, but are not limited to, homobifunctional linkers and heterobifunctional linkers. As an illustrative example, a linker may comprise a carboxylic acid that has been activated by conversion to its acid chloride to react with an amino acid (e.g., lysine) residue of a binding molecule comprising a monoclonal antibody, and a thiol reactive group to link with the particle or the Raman-active reporter molecule.

Heterobifunctional linkers are well known to those skilled in the art and generally contain a functionality on one end that binds to a target (e.g., a molecule or surface), and an opposite end having a second reactive functionality to specifically link to a different target. Heterobiofunctional photo-reactive linkers (e.g., phenylazides containing a cleavable disulfide bond) are also well known in the art and may be employed as linkers in accordance with the present invention. For example, a sulfosuccinimidyl-2-(p-azido salicylamido)ethyl-1,3'-dithiopropionate contains a N-hydroxy-succinimidyl azide (upon photolysis) reacts with any amino acid.

The linker may further comprise a protective group which blocks reactivity with a functional group on the linker which is used to react with and bind to a molecule or particle to be linked. A deprotection reaction may involve contacting the linker to one or more conditions and/or reagents which remove the protective group, thereby exposing the function group to interact with the molecule to be linked. Depending on the nature of the protective group, deprotection can be achieved by various methods known in the art, including, but not limited to, photolysis, acidolysis, hydrolysis, and the like. Depending on such factors as the molecules and particles to be linked, and the conditions in which the method of detection is performed, the linker may vary in length and composition for optimizing such properties as flexibility, stability, and resistance to certain chemical and/or temperature parameters. For example, short linkers of sufficient flexibility include, without limitation, linkers having from 2 to 10 carbon atoms (see, e.g., U.S. Pat. No. 5,817,795).

Any two molecules having an affinity for each other may comprise the reagent/analyte complex according to the present invention. Examples of ligand-binding systems include: antibodies and antigens; hormones and their receptors; lectins and the complex carbohydrates to which they bind; effector molecules and their receptors; complimentary nucleotide sequences; binding molecules designed through molecular modeling and synthesized specifically to bind another molecule, and molecules with mutual affinity to each other, such as avidin and biotin.

In one embodiment, the Raman-active reporter molecule and the binding molecule are each independently linked to the surface-enhancing particle. The Raman-active reporter molecule and the binding molecule may be either directly linked to the surface enhancing particle or indirectly linked to the surface enhancing particle by way of a linker molecule.

In another embodiment, the binding molecule is operably linked to the Raman-active reporter molecule, which is operably linked to the surface enhancing particle. The Raman-active reporter molecule and the binding molecule may be either directly linked to the surface enhancing particle or indirectly linked to the surface enhancing particle by way of a linker molecule.

The Raman-active reagents of the present invention may be manufactured in the lab or provided to the user in the form of a kit. The kit may include a previously prepared Raman-active reagent, or the ingredients for manufacturing the Raman-active reagents as described above. The kit may also include ingredients that minimize nonspecific binding (nonspecific binding ingredient) and ingredients that stabilize the reagent (stabilizing ingredient) to extend its shelf life. Various nonspecific binding ingredients and stabilizing ingredients effective in use with the present invention are well known in the art. In addition, the kit may include a capture substrate covered with binding molecules to immobilize analytes for subsequent detection with the Raman-active reagent. For the simultaneous detection of multiple analytes, the kit may also include unreactive spacer molecules, such as molecules terminated with ethylene glycol units, for interspersing amongst the binding molecules so as to minimize steric interferences as well as to resist nonspecific adsorption. For example, surfactants, blocking agents, and buffers may be added.

Raman reporter-labeled immunogold probes can be prepared in many different ways. For example, as depicted in FIG. 1(a) (the co-immobilization approach), an uncoated gold nanoparticle is labeled with Raman-active reporter molecules through the spontaneous adsorption of thiol-containing reporter molecules on gold, and then integrated with antibodies. The amount of thiol is chosen to coat only a portion of the nanoparticle surface and to leave exposed portions of the nanoparticle surface available for antibody immobilization. The antibodies are subsequently immobilized on the uncoated portion of the reporter-labeled nanoparticle through a combination of ionic and hydrophobic interactions. Immobilization can, of course, also be achieved by simply adsorbing an antibody directly on a coating of Raman-active reporter molecules.

In a second example, as depicted in FIG. 1(b) (the covalent linker approach), an uncoated gold nanoparticle is labeled with Raman-active reporter molecules, which are then covalently linked to antibodies. The Raman-active reporter molecule not only carries thiol or disulfide groups for immobilization on the gold nanoparticle, it also contains a succinimide ester functional group (i.e., a coupling reagent) for the covalent linking of an antibody. The covalent linker approach enhances the Raman reporter coverage and ultimately its sensitivity. Because the antibodies are covalently linked to the nanoparticles, the exchange of antibodies between nanoparticles with different Raman reporter molecules is reduced, and hence the probe specificity in the multi-analyte application is improved.

The Raman-active reagents of the present invention determine the presence or amount of a target analyte, if present in a test sample, by the binding specificity of the binding molecule for the target analyte, or a portion thereof, and the generation and measurement of a SERS signal induced by the application of electromagnetic radiation onto the reagent/analyte combination. The Raman-active reagents may be used in clinics or forensic labs for the detection of drugs, pesticides, microbial toxins, hormones and biologically important proteins, industrial chemicals, explosives, pesticides, chlorophenols and other pollutants in soils, water, air, biological materials and other matrices. Such analysis may include in-situ testing methods (i.e., those not requiring any separation of the analytes from the sample prior to either their analysis or detection), as well as other in vivo, in vitro, or ex vivo methods.

The detection or measurement of target analytes using the Raman-active reagents according to the present invention may be performed using any one of a number of assaying techniques known in the art. In general, a test sample is placed in contact with a Raman-active reagent of the present invention under suitable conditions to allow the binding molecule to specifically bind to the target analyte, thus forming a reagent/analyte complex. The sample containing the reagent/analyte complex is then exposed to an excitation source (e.g., light source) that is suitable for exciting the Raman-active reporter molecule to induce surface enhanced Raman scattering. The intensity of the Raman scattering signal can then be measured to determine the presence or amount of the target analyte in the test sample. Absence of a Raman scattering signal is indicative of the absence of the target analyte in the test sample.

Techniques for detecting Raman scattering are well known in the art. The primary measurement is one of light scattering intensity at particular wavelengths. Neither the angle of the incident beam nor the position of the detector is critical. With colloidal suspensions, detection is often at an angle of 90° to the incident beam. The intensity of the Raman scattering signals must be measured against an intense background from the excitation source. As such, the use of Raman-active report molecules with large Stokes shifts is preferred.

Several devices are suitable for collecting SERS signals, including fiber-optic waveguides, wavelength selective mirrors, and holographic optical elements for scattered light detection. The choice of the detector will largely depend on the sensitivity of detection required to carry out a particular assay. The intensity of the signal may be measured using a silicon photodiode, a charge coupled device (CCD), photographic film, or photomultiplier tubes arranged either singly or in series for cascade amplification of the signal. Photon counting electronics can also be used for sensitive detection.

Analysis of the SERS spectrum will typically include the use of some form of data processor such as a computer. Raman signals consist of a series of distinct spectral lines of varying intensity. The frequencies and relative intensities of these spectral lines are specific to each Raman-active reporter molecule being detected such that each Raman-active reporter has a distinct "fingerprint". The manner in which this fingerprint is analyzed will depend primarily on the purpose of the detection. If a SERS analyzer is being used to selectively detect one or more analytes out of a test sample containing multiple analytes, then an analysis of the entire fingerprint for each reporter molecule may be necessary to make a reliable identification. However, if the analyzer is being used to quantify the detection of one or several labels, each of which has a unique spectral line, then an analysis of only the unique spectral line may be necessary.

The excitation source may be any source capable of exciting the Raman-active reporter molecule to induce Raman scattering. Typically, excitation will be carried out using incident light from a laser having a frequency in the visible spectrum. However, it is possible to envision situations in which other frequencies might be used, for example, in the ultraviolet or near-infrared ranges. The selection and tuning of the excitation source, with the appropriate frequency and power, will be well within the capabilities of one skilled in the art and will depend on the reporter molecule, surface enhancing particle and target analyte employed. In the preferred embodiment, a laser serves as the excitation source. The laser may be an inexpensive type such as a helium-neon or diode laser. Preferably, a diode laser is used at or near the IR spectrum, minimizing fluorescence interference. Lamps may also be used as the excitation source. Direct illumination of the surface or by evanescent waves from a waveguide beneath the plasmon-active surface may also employed to induce a SERS affect.

Figure 5:
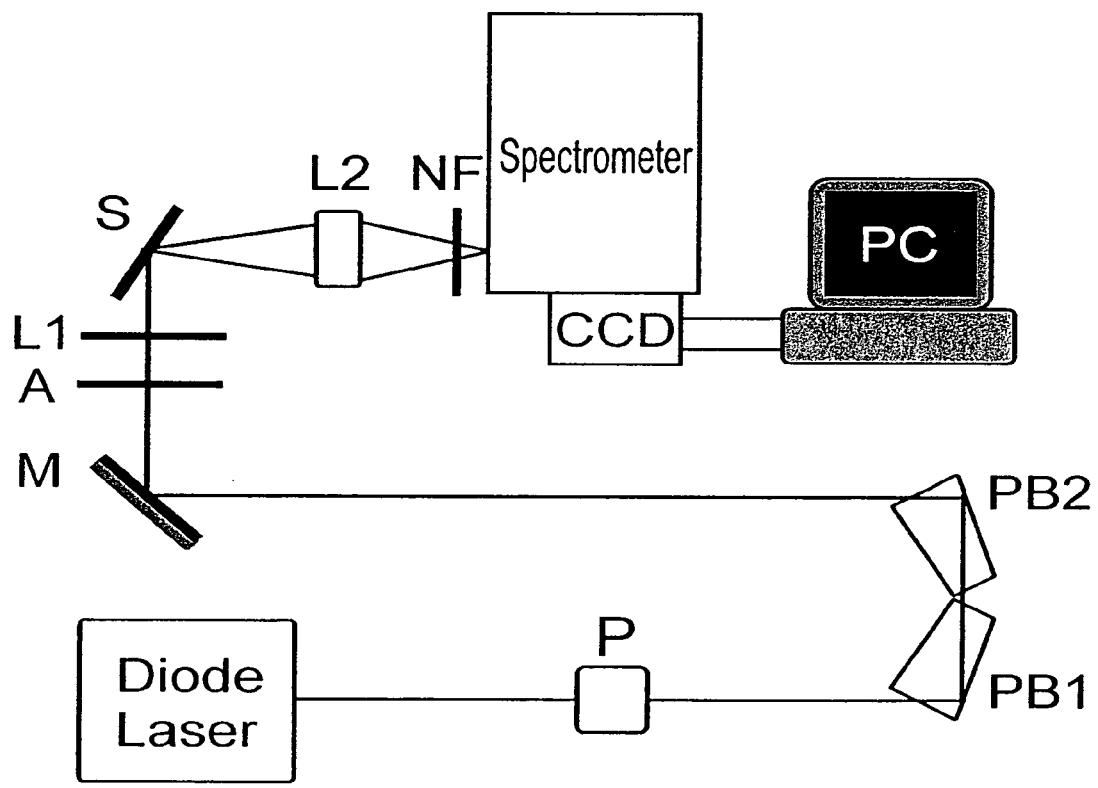
FIG. 5 depicts an illustrative setup for SERS measurements. P: polarization rotator; PB 1 and PB2: Pellin Brocha prisms; M: mirror; A: aperture; L1: cylindrical lens; S: sample slide; L2: collection lens; NF: notch filter.
Figure 6:
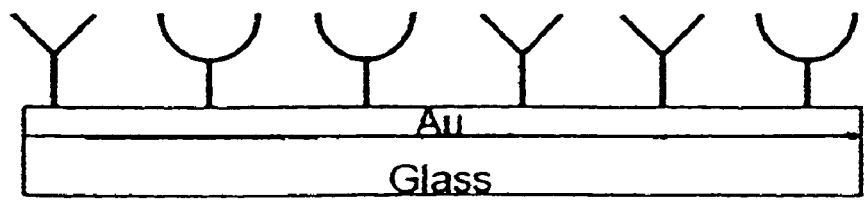
FIG. 6 illustrates an example of a sandwich assay employing Raman-active reagents of the present invention.
Figure 6:
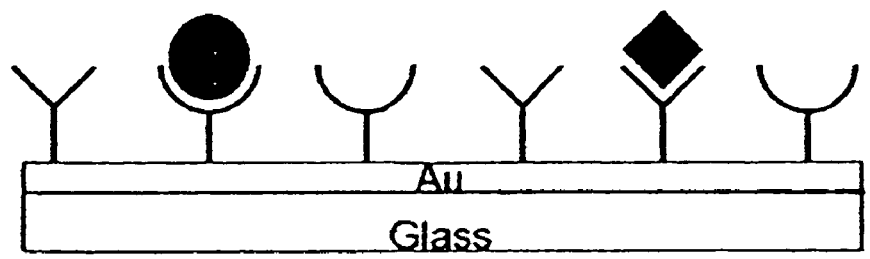
Figure 6:
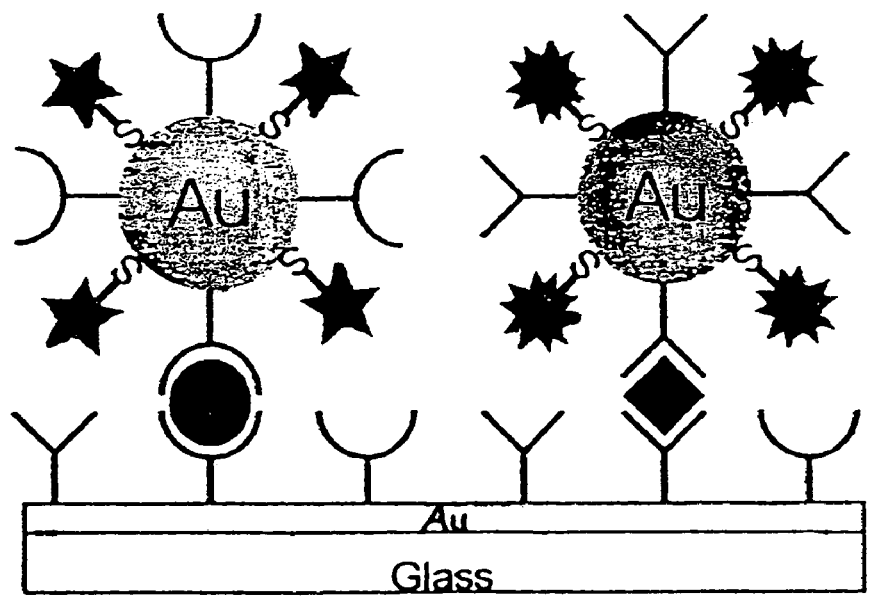
Figure 6:
Figure 6:
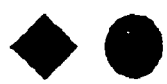
Figure 6:
Figure 7:
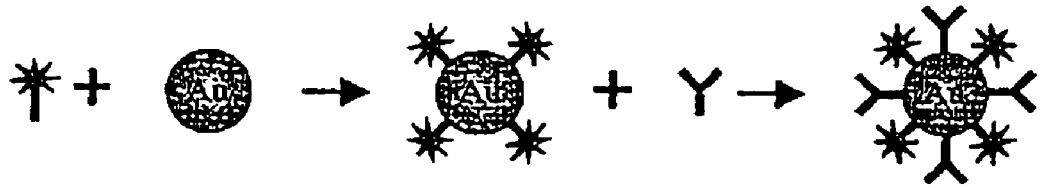
FIG. 7 is a schematic that comparatively illustrates two methods for preparing Raman-active immunogold reagents: (a) tracer nanoparticles are prepared by the physisorption of antibodies on gold colloids that had been previously coated with a partial monolayer of RRMs (Raman reporter molecules) based on aromatic thiols; (b) produces particles coated with a thiolate-based monolayer that has a terminal succinimide group (i.e., a terminal reactive functional group). This schematic (b) shows that the terminal succinimide group can then react with the amines of a protein to form an amide linkage.
Figure 7:
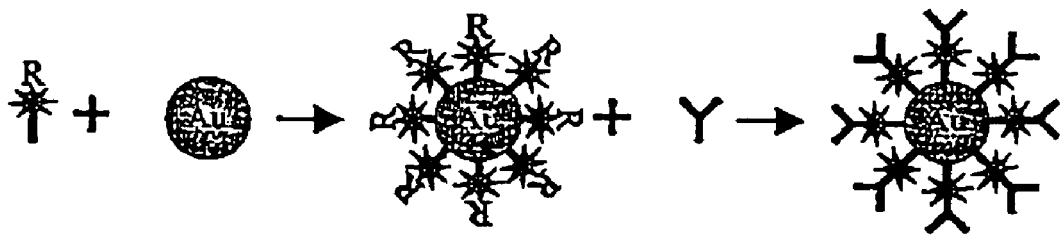
Figure 7:
Figure 7:
Figure 7:
Figure 7:

An illustration of a typical SERS measurement system is depicted in FIG. 5.

Figure 3:
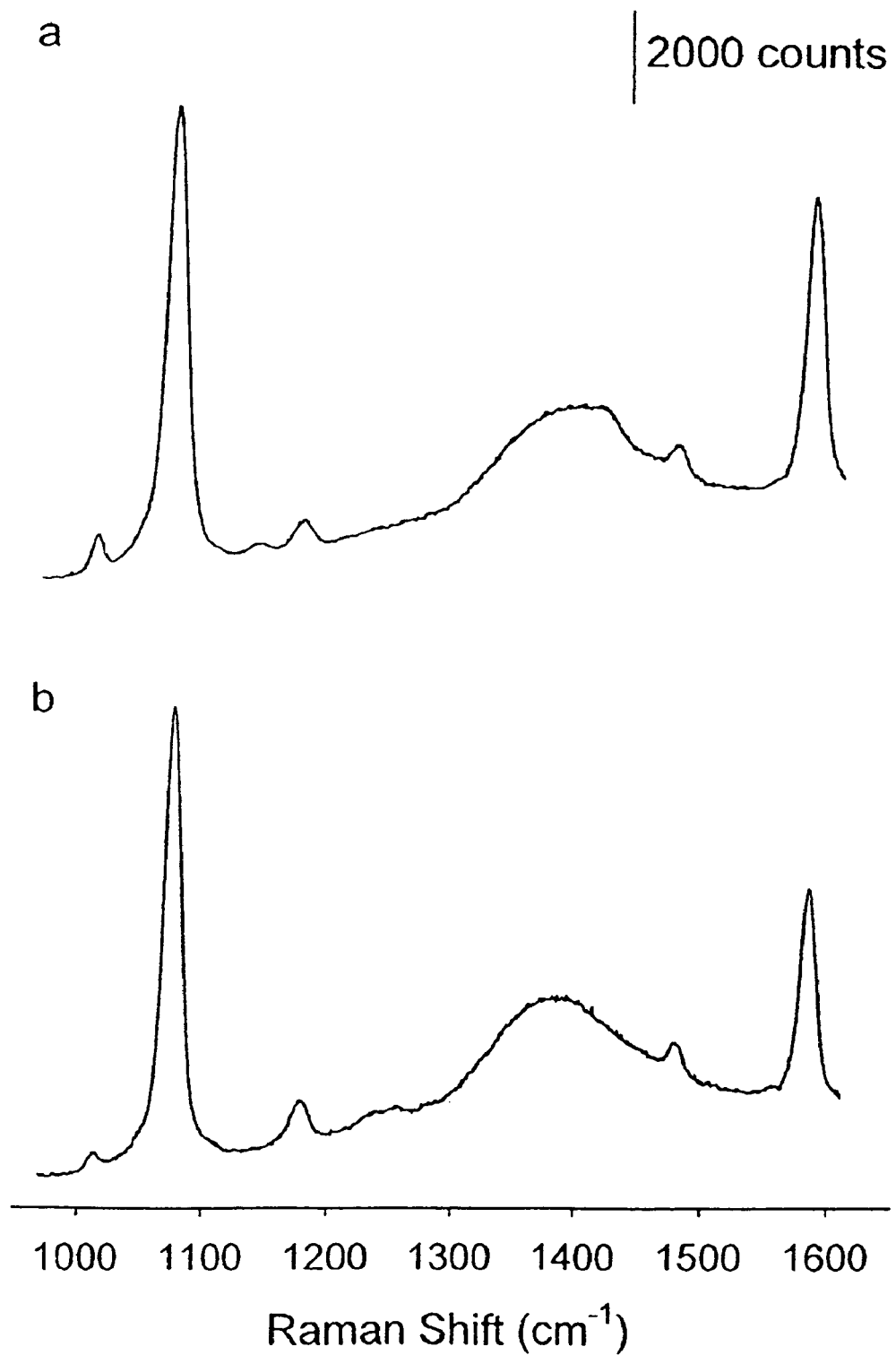
FIG. 3 is a graph illustrating the SERS spectra of dithiobisbenzonic acid (DBA) and 4,4'-dithiobis(succinimidylbenzoate) (DSB) Raman-active reporter molecules adsorbed on gold island film substrates: (a) DBA, (b) DSB.

In the preferred embodiment, the test sample may be placed in contact with a capture substrate covered with binding molecules that selectively immobilize analytes for subsequent detection with the Raman-active reagent. This substrate is then treated with the Raman-active reagent under suitable conditions to allow the Raman-active reagent binding molecule to specifically bind to the target analyte, forming the reagent/analyte complex. FIG. 3 illustrates one type of assay employing such a method. In this example, a different Raman-active reporter molecule is associated with a different antibody as different probes, with the presence of different antigens detected by the characteristic Raman bands of the reporters. In an alternative embodiment, the test sample may be contacted with the Raman-active reagent under suitable conditions to allow the Raman-active reagent binding molecule to specifically bind to the target analyte, forming the reagent/analyte complex, prior to its capture by the substrate.

The substrate may take the form of a generally flat surfaces (e.g., strips, slides, gene chips, etc.) or inert support structures of silica, carbon, plastic, glass, paper or other materials which may be in the form of macroscopically flat or textured pieces, slides, strips, spheroids or fibers capable of supporting the reagent/analyte complex. Analytes and/or the reagent/analyte complex may bind to the substrate by direct adsorption, adsorption through a linker covalently attached to either the particle or the reporter molecule, by covalent attachment of the particle or reporter molecule to the substrate directly or through a linker or by intercalation of the distal portion of the linker into the substrate surface, by magnetic attraction to the substrate, or by specifically binding a second binding molecule affixed to the substrate to the target analyte or a molecule operably linked to the particle and having a specific affinity for the second binding molecule. For example, the substrate may include a binding molecule identical to that found on the Raman-active reagent that binds the target analyte, such as in a sandwich assay. Such a system might be employed for the detection of multiple target analytes using a limited number of different Raman-active labels in association with multiple binding molecules. Identification and quantification of the analytes would be accomplished through the measurement of the distinctive spectral fingerprints of the Raman-active labels provided for each analyte. Alternatively, the substrate may contain address locations for the various analytes with the specific binding molecule identified by the address location rather than by its spectral fingerprint. This system may also be employed for separating the target analyte from the test sample.

In another embodiment, the method may further comprise exposing the test sample to a magnetic force that separates the reagent/analyte complex from the test sample. Such separation may occur if the surface-enhancing particle comprises of a material that is responsive to a magnetic force. In this case, the magnetic-responsive material is likely to be coated with a metallic material capable of emitting a SERS signal. Upon detection of the SERS signal, the magnetic force may be applied to cause the reagent/analyte complex to be separated from the test sample. In addition, different Raman-active reagents having different Raman-active reporter molecules and binding molecules may be employed to allow for the sorting of multiple target analytes using magnetic forces.

Assay kits for the method of the present invention are also provided. In one preferred embodiment, the assay kit comprises a Raman-active reagent in accordance with the present invention, wherein the Raman-active reagent includes at least one binding molecule having an affinity for a known target analyte. In a second embodiment, a substrate capable of binding the analyte and/or the reagent/analyte complex is provided. For the simultaneous detection of multiple analytes, the kit may also include unreactive spacer molecules, such as molecules terminated with ethylene glycol units, for interspersing amongst the binding molecules so as to minimize steric interferences as well as to resist nonspecific adsorption. For example, surfactants, blocking agents, and buffers may be added.

One aspect of the present invention is that it allows multiple target analytes to be detected from a single test sample. For example, simultaneous detection may be achieved by the use of multiple binding molecules, each specific to a target analyte or a class of target analytes and each associated with a different Raman-active reporter molecule. Because Raman-active vibrational modes usually yield bands one to two orders of magnitude narrower than most fluorescence bands, it is now possible to distinguish a much large number of different Raman labels as compared to fluorescent labels. Alternatively, a single Raman-active reporter molecule may also be employed with identification based on an address location on a substrate, such as a gene chip or screening slide, as is well known in the art.

Because Raman scattering is not affected by oxygen and other quenchers, thus simplifying its use in many different experimental environments, it has potential advantages as a broadly applicable readout method in comparison to the widely used fluorescence detection schemes. In addition, because the SERS signal is less subject to photobleaching, lower detection limits can be obtained by increasing the signal integration time. Raman-active vibrational modes also usually yield bands one to two orders of magnitude narrower than most fluorescence bands, indicating the possibility of distinguishing a much large number of different Raman-active labels than likely with fluorescent labels, and minimizing the need to use spacial locations for analyte identification.

One argument favoring a fluorescence over a Raman-based detection scheme, in the past, is the inherent detection capability of fluorescence measurements. However, by combining the SERS effect and the use of reporter molecules with a relatively large Raman scattering cross section as extrinsic labels, trace amounts of intrinsically weak Raman scatterers (e.g., antibodies) can be indirectly detected. A detection limit of 0.1 pg/mL has been estimated from recent experiments for the antibody detection. With further optimization, even lower detection limits are expected. This will include using dyes for Raman reporter molecules that absorb the Raman excitation light. This leads to surface enchanced resonance Raman scattering or SERRS. SERRS can be 2-6 orders of magnitude stronger than SERS. It is important to note that in the present invention, the reporter molecules are directly attached to the metal nanoparticle surface, which effectively quenches potential fluorescence from the reporter molecule that could interfere with the Raman measurements.

The below Examples include an illustration describing an application of one type of Raman-active gold colloidal reagent (Raman-active reagent) used as a detection reagent in immunoassays. It is envisioned that similar concepts can be developed for other types of assays, target analytes and Raman-active reagents developed in accordance with the present invention, as well as infrared-active colloidal reagents, and in some cases, reagents for fluorescence or electrochemical based assays.

The following examples are provided as further non-limiting illustrations of particular embodiments of the invention.

EXAMPLES

Example 1

Synthesis of Raman-Active Reporter Molecule 4,4'-dithiobis(succinimidylbenzoate)

The Raman-active reporter molecule 4,4'-dithiobis(succinimidylbenzoate) (DSB) was synthesized following a procedure similar to that used for preparing dithio-bis(succinimidylundecanoate) as described in Wagner et al., *Biophys. J.* 1996, 70, 2052, which is incorporated herein by reference. Briefly, 0.50 g of the reporter molecule dithiobisbenzonic acid (DBA) (1.6 mmol) (Toronto Research Chemicals, Inc), 0.67 g of 1,3-dicyclohexylcarbodiimide (DCCD) (3.2 mmol) (obtained from Aldrich), 0.37 g of N-hydroxysuccinimide (NHS) (3.2 mmol) (obtained from Aldrich), and 60 mL of tetrahydrofuran were added to a 100 mL round-bottom flask equipped with a magnetic stir bar and drying tube. The reaction mixture was stirred at room temperature for three days. The solution was then filtered and the solvent was removed under reduced pressure to give an orange residue. The crude product was dissolved in hot acetone and filtered again. Hexane was added to the filtrate until the solution became cloudy and the product was obtained as an orange powder. H-NMR (300 MHz, CDCl$_3$): δ 8.08 (d, 4H), 7.60 (d, 4H), 2.91 (s, 8H). Infrared reflection spectroscopy: 1810 cm$^{-1}$ ($v_{(C=O)}$ of the ester), 1772 cm$^{-1}$ ($v_{s(C=O)}$ of the succinimide), 1746 cm$^{-1}$ ($v_{as(C=O)}$ of the succinimide), 1585 cm$^{-}$($v_{(C=C)}$ of the benzene ring).

Example 2

Preparation of Raman-Active Reagents Using Co-Immobilization

Raman-active immunogold colloidal reagents were prepared using the co-immobilization approach depicted in FIG. 1(a). First, 25 μL of ethanolic Raman reporter solution (0.5 mM DBA) was added to 10 mL of a suspension of uncoated gold colloids (~30 nm diameter, 2×10$^{11}$ particles/mL) (Ted Pella, Inc.). The mixture was allowed to react for 5 hours at room temperature. During this step, the reporter molecules bound via self-assembly onto the colloid surface through the formation of sulfur-gold linkages. We note that this amount of reporter, based on an estimation of the colloidal surface area, will only partially cover the colloid, leaving portions of the uncoated colloidal surface available for protein immobilization. After separating the reporter-labeled colloids from solution by centrifugation at 14,000 g for 4 minutes, the loosely packed, red-colored sediment was resuspended in 10 mL of borate buffer (2 mM, pH 9).

The Raman-active colloids were next immuno-labeled by adding 230 μg of goat anti-rat IgG to 10 mL of the above suspension. The mixture was incubated at 4° C. for 12 hours, during which the IgG protein adsorbed directly onto the exposed colloidal surface through a combination of ionic and hydrophobic interactions. The incubation was followed by centrifugation at 14,000 g for 5 minutes, and the loose sediment of reporter-labeled immunogold was rinsed by resuspending in 2 mM borate buffer and collected after a second centrifugation. Finally, the labeled colloids were suspended in 10 mM tris(hydroxymethyl) aminomethane (Tris)-buffered saline (Tris/HCl, NaCl 10 mM, pH 7.6) giving a concentration of approximately 2×10$^{11}$ particles/mL. Tween 80 (1%) (Aldrich) was also added to the suspension to minimize non-specific adsorption in the assays. The suspensions usually remained uniformly dispersed for 2-3 days when stored at 4° C.

Example 3

Preparation of Raman-Active Reagents Using a Covalent Linking

Raman-active immunogold colloidal reagents were prepared using the covalent linking approach depicted in FIG. 1(b). The DSB molecules were used as both Raman reporters and antibody linkers. The succinimide ester group of the DSB molecule can readily react with the primary amine group of an amino acid, such as the lysine, present in antibodies such as IgG to form a covalent bond. As shown in Scheme 2, the preparation of the covalently-linked colloidal reagent follows a process very similar to that used for the co-immobilized reagents. However, with the covalent linking approach, the antibodies indirectly attached to the colloid through the reporter molecules rather than directly adsorbed onto the colloidal surface. Briefly, 25 μL of a reporter-linker solution (5 mM DSB in CHCl$_3$) was added to 10 mL of bare gold suspension (30 nm) under vigorous agitation. The molecules self-assemble onto the colloid surface, with their succinimide end groups available for protein immobilization. It is noted that this amount of the reporter-linker is estimated to be more than enough to cover the entire colloidal surface. The reporter-linker labeled colloids were centrifuged, and resuspended in the aforementioned borate buffer.

Similar to the co-immobilization approach above, 230 μg of goat anti-rat IgG were added to the 10 mL suspension of the DSB-labeled gold colloids, followed by an incubation at 4° C. for 12 hours. This step covalently couples anti-rat IgG molecule to the colloid surface via amide linkages that are formed by the reactions of its amine groups with the succinimide ester groups of DSB. Finally, the Raman-active immunogold was rinsed and resuspended in Tris buffer, and the final concentration of the colloids was adjusted to approximately 2×10$^{11}$ particles/mL. The suspensions were usually stable for a few weeks when stored at 4° C.

Example 4

UV-Vis Characterization of Gold Island Films

Gold island films were used as SERS-active substrates to examine the scattering properties of the acid-terminated DBA and succinimide-terminated DSB reporters discussed above. Gold films were deposited onto clean glass microscope slides by resistive evaporation at a pressure of less than 1.3×10$^{-4}$ Pa. Gold island films, which were used as the SERS substrates in Raman reporter characterization experiments, were prepared by evaporating approximately 5 nm of gold directly onto the glass substrate. The island films were then derivatized with reporter molecules by immersion in 1 mM DBA (in ethanol) or 1 mM DSB (in chloroform) solutions for 24 hours, and subsequently rinsed with the corresponding neat solvents before SERS characterization. Smooth gold films were prepared by first coating a glass substrate with 15 nm of chromium followed by 300 nm of gold. These substrates were used to prepare capture antibody substrates for the immunoassay experiment described below.

Figure 4:
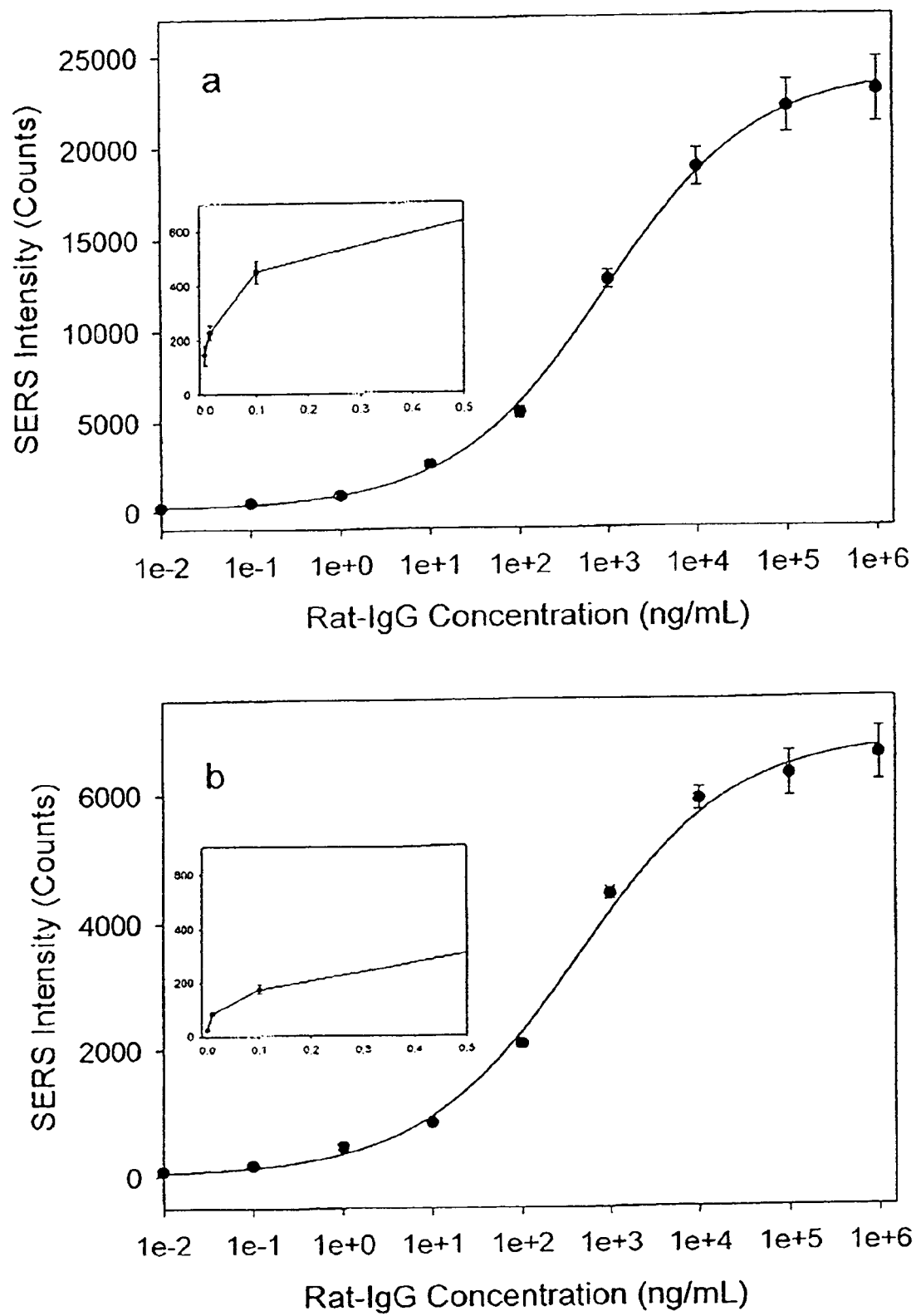
FIG. 4 is a graph illustrating the dose-response curves of the intensity of the strongest SERS band (1075 $cm^{-1}$) versus the rat IgG concentration: (a) using the colloidal detection reagent prepared via the co-immobilized approach, (b) using the colloidal detection reagent prepared via the covalent linking approach.

To minimize differences caused by substrate variability, the gold island films (~5 nm thick) were first examined using UV-Vis spectrometer. FIG. 4 shows the spectra of two such films (spectra a and b) before immersion in the reporter molecule solution. For comparison, spectrum c was collected from 5 nm colloidal gold suspended in aqueous solution. Both island films exhibited a plasmon resonance band with a maximum of 597 nm, while that for colloidal gold was at 519 nm. The plasmon bands from the island films were also wider than that observed from uniformly dispersed 5 nm colloidal gold. The difference in the spectra of the 5 nm-thick gold island films and the 5-nm diameter gold colloid suspension can be explained by the distribution of sizes and shapes of the nanostructures on the two different types of samples. Evaporated gold islands usually have a broad size distribution with different irregular shapes. Colloidal gold, on the other hand, is reported to be more uniform in size and have a near-spherical shape.

It is more important to note that the spectra for the two island films were effectively superimposable. This agreement argues that the average sizes and shapes of the islands on the two substrates were strongly similar. As a result, both substrates should have had similar surface plasmon properties and therefore produce similar magnitudes of surface enhancement for Raman scattering.

Example 5

SERS Characterization of DBA and DSB Reporter Molecules

Figure 2:
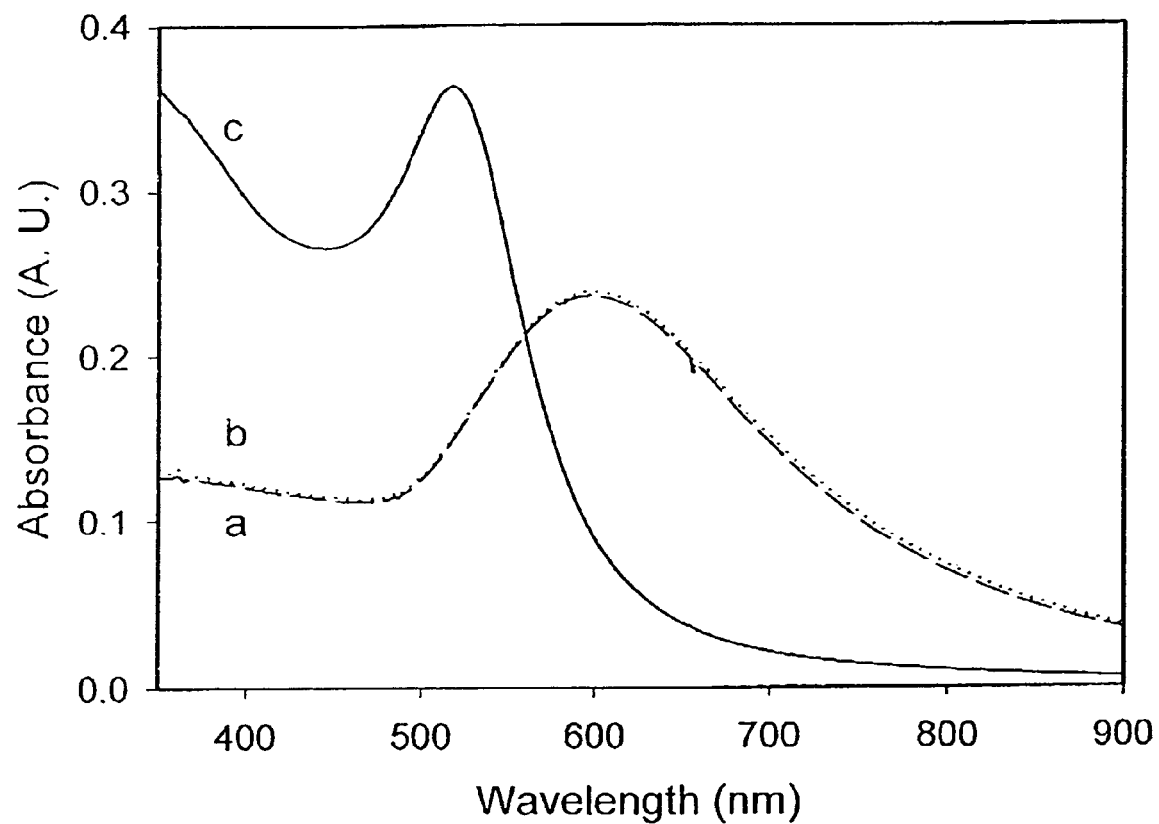
FIG. 2 is a graph illustrating the UV-Vis spectra for SERS substrate characterization.

The DBA and DSB reporter molecules were analyzed to determine the difference in the reporter scattering properties as a result of altering the terminal functional groups in the reporter molecule. The experimental setup for the SERS measurements is shown in FIG. 2. The signal was excited with a diode laser (Hitachi HL7851G, Thorlabs) operated at 20° C. and 120 mA. These conditions produced 50 mW of output power at the sample with a wavelength of 785.13 nm. A polarization rotator adjusted the polarization direction of the laser to minimize reflection losses at the Pellin-Brocha prisms. The prisms were used to remove background laser emission. The laser beam was then directed by a mirror through an aperture and focused by a 50-mm focal length cylindrical lens to a 3 mm by 0.25 mm line on the sample surface. The laser beam irradiated the sample at an angle of approximately 60° with respect to the surface normal, and the scattered light was collected and focused onto the entrance slit of the monochromator with a$f$/2 lens. A holographic notch filter (HSPF-785.0, Kaiser Optical Systems) was used to block the Rayleigh scattered light, while the Raman scattered light passed through the entrance slit (200 µm slit width) of a 300 f/4 spectrograph (SpectraPro 300i, Acton Research Corp.) and illuminated onto a 1200 grooves/mm grating. The grating was blazed for 750 nm and produced a nominal dispersion of 2.7 nm/mm. A thinned, back-illuminated, liquid nitrogen-cooled CCD (LN/CCD-1100PB, Princeton Instruments) was controlled by a PC for spectra acquisition. The positions of the reporter molecule Raman bands were determined by calibration using the known band positions of solid naphthalene.

SERS spectra (10 second integration time) of self-assembled monolayers of DBA and DSB on the gold island films are shown in FIG. 3. Several strong aromatic vibrational bands from the benzene ring are present within this spectral region. The strongest band at 1075 $cm^{-1}$ is from the aromatic C—H in-plane bending, and another major band at 1585 $cm^{-1}$ is from the C=C ring stretching. To obtain maximum sensitivity, signals at 1075 $cm^{-1}$ were used as readout in both the DBA and DSB-based immunoassays. The similar intensities of the bands in the two spectra of FIG. 3 was consistent with what was expected based on the similarity in the molecular structures of the two types of reporters. It was also noted that the intensity ratios of the peak at 1075 $cm^{-1}$ to the peak 1585 $cm^{-1}$ in the two spectra were slightly different, possibly reflecting the orientation difference of the two types molecules when adsorbed on the surface.

The existence of two additional bands was observed in the DBA spectrum, both with very low intensities. The band at 1420 $cm^{-1}$, which appears as a shoulder on the broad glass band (i.e., Si—O stretches) around 1390 $cm^{-1}$, is strongly characteristic of a $COO^-$ symmetric vibration, while the 1150 $cm^{-1}$ band in the DBA spectra is tentatively assigned to a C—OH stretching mode. In summary, replacing the carboxylate group with succinimide group had only a minor influence on SERS signal derived from the benzene structure in the DBA and DSB molecules. The Raman signatures from the carboxylate group diminished in the DSB spectrum, verifying the synthesis product.

Example 6

Preparation of Capture Antibody Substrates

Glass microscopes slides were soaked in a dilute surfactant solution (Micro, Cole-parmer) for 12 hours, rinsed with deionized water and ethanol, and dried in a stream of nitrogen. The slides were then coated with 15 nm of chromium, followed by 300 nm of gold by resistive evaporation at a pressure of less than $1 \times 10^{-4}$ Pa. The gold substrates were next cut into 1 cm×1 cm sections and immersed in a 1 mM ethanolic solution of thioctic acid for approximately 12 hours to form a carboxylic acid-terminated monolayer.

The immobilization of the IgG proteins was accomplished by first immersing the monolayer-modified substrates into 1% (w/w) 1-ethyl-3-[3-(dimethylamino)propyl] carbodiimide (EDC) (Aldrich) in anhydrous acetonitrile for 5 hours. This step activates the free carboxyl groups of thioctic acid by forming on O-acylurea intermediate with the EDC. The activated surface was then modified with capture antibody by pipetting 100 µL of goat anti-rat IgG (100 µg/mL, 0.1 M borate buffer, pH 9) (Pierce) onto approximately 1-$cm^2$ of the activated substrate. This reaction was allowed to progress at 4° C. for 12 hours. Finally, the antibody-coated substrates were rinsed with deionized water, and quickly dried under a stream of argon. All assays were conducted using freshly prepared substrates.

Example 7

Dose-Response Curves

Dose-response curves were constructed based on the results of a set of sandwich assays. Samples containing Rat IgG (Pierce) as a model antigen were prepared at concentrations ranging from 0.01 ng/mL to 1 mg/mL in 50 mM PBS buffer ($KH_2PO_4$/$K_2HPO_4$, 150 mM NaCl, pH=7.6). A 100 µL aliquot of each sample solution was pipetted onto the separate capture antibody substrates described above, and allowed to react for 1 hour at room temperature. After rinsing with copious amounts of water, the substrates were then exposed to 100 µL of reporter-labeled immunogold solution for 3 hours. All substrates were rinsed with deionized water and dried under argon before SERS characterization.

The detection approach relied solely on the SERS effect by utilizing the immunogold colloids labeled with Raman-active reporter molecules as detection reagents. In this approach, gold colloids were labeled with both antibodies for bio-recognition and Raman-active reporter molecules for signal transduction. A key feature of this concept is that the scattering center of the label is positioned in close proximity to the colloid surface, which strongly enhances the signal. The presence of the antigen was therefore recognized by its detection antibody, and the SERS signal of the co-immobilized Raman active species reported the ligation of the antibody with the antigen.

The strongest SERS band at 1075 $cm^{-1}$ was used as readout in the immunoassay experiments. FIG. 4 plots the intensity of this band versus the concentration of the antigen, rat IgG, with either the co-immobilized (4a) or the covalently-linked colloids (4b) as detection reagent. In both experiments, SERS signals show proportional response to the antigen concentration almost over the entire tested concentration range, representing a dynamic range of nearly 8 orders of magnitude. The solid lines represent the curve fitting of the immunoassay data based the four-parameter logistic model, a common regression model used for describing sandwich type immunoassays. The slope of the curve suggests how the readout signals quantify samples of different concentration; the larger the slope, the easier the distinction. Two important parameters obtained from the curve fitting will be discussed with more details in the later sections. One is the expected signal at zero dose, which is also called the negative control signal, the other is the expected signal at infinitely high or saturation dose, which is also called the positive control signal.

When working with samples at low concentration, we found it was more difficult to distinguish the analyte signal (S) accurately from that at zero dose than from the spectral noise (N). For example, even the signals from the negative control samples, were readily distinguishable from the noise in the spectra with S/N larger than 3 in both experiments. We therefore defined the limit of detection (LOD) as the concentration associated with a response three times the mean response obtained at zero dose. The LOD was around 0.2 ng/mL when employing the co-immobilized reagent, but lowered to 0.04 ng/mL with the use of the covalently-linked reagent.

The difference in LOD was largely due to the different SERS intensities observed for the two negative control samples, which were obtained through the same assay procedure, using samples at a concentration of zero (i.e., buffer only). Indeed, the difference in the negative control signals, which reflect different extents of nonspecific binding, is a major difference between the two sets of results. The colloidal reagent prepared using the co-immobilization approach seemed to yield a more pronounced nonspecific binding, and therefore, a higher Raman signal (145 counts) for the negative control sample (from curve fitting, S is 164 counts at zero concentration). In comparison, the colloids modified via the covalent linking approach yielded a much lower signal (22 counts) from the negative control (32 counts based on curve fitting). Because of the lack of a fluorescence background and lack of photobeaching of the Raman-active reagent, LOD values could be lowered by increasing the signal integration times.

Scanning Electron Microscopy images of these sample surfaces showed that a higher colloid density was observed on the capture antibody substrate when using the co-immobilized reagent, supporting the conclusion that a higher extent of nonspecific binding occurs with these samples. The increased nonspecific binding of the co-immobilized colloids was attributed to the weak interaction between the antibody and the colloid surface. This interaction is weakened due to the partial coverage of the reporter molecules on the colloid surface, which reduces the surface area on a colloid that can interact with the antibody and hence weakens the binding. This weak interaction can result in vacancies on the reporter-labeled immunogold colloid, and lead to its nonspecific binding with the antibodies on the capture substrate. Covalent coupling reduces this complication, which in turn, lowers the amount of nonspecific binding.

In addition to the negative control signal, all the spectra obtained with the covalently-linked colloidal reagent were of lower intensity than those obtained with the co-immobilized colloid for samples of same concentration. Based on the characterizations on the gold island film in FIG. 5, it is not believed that the lower intensity observed with the covalently-linked immunogold is due to the difference in the Raman scattering intensity between the DSB and DBA molecules. It is suspected that the lower signal in FIG. 4(b) may arise from an increased extent of antibody denaturation due to covalent linking, which lowers the "active" detection antibody levels on the colloid surface.

It is important to note that, although the co-immobilized colloids yielded much higher absolute Raman signals, the relative signals that normalized to the signal at zero dosage were always higher when using the covalently-linked reagent for detection. The curve fitting results show, for example, that the expected signal at the saturation dosage for the co-immobilized reagent is almost 2.5 times higher than that obtained using the covalently-linked reagent. However, the ratio for the signals at saturation dosage with respect to those at zero dosage is 50% larger for the covalently-linked reagent. The higher ratio suggests a sharper contrast between the positive and the negative control signal and therefore a more accurate distinction between an analyte and a blank sample.

The colloidal suspension prepared from the covalent linking approach was also more stable in solution and less susceptible to aggregation. These observations explain the lower run-to-run variation observed when using the covalently-linked reagent (~10%) compared to that when using the co-immobilized reagent (>20%). It was also noted that when starting with a new batch of reporter-labeled immunogold reagent, the batch-to-batch variation was even more significant and sometimes up to 100% when using the co-immobilized reagent. It is suspected that this difference represents the importance of the first step in the colloid modification. It is less critical in the covalent linking approach because DSB was always added at a level to ensure the exhaustive coverage of the reporters on every colloid. However, it is very critical in the co-immobilization approach since the dosage of DBA determined the reporter coverage on each colloid and hence the signal intensity per colloid.

Example 8

Reagents Used in Preparation of Raman-Active Molecules

Suspensions of unconjugated colloidal gold (32.2+4.4-nm diameter, $2 \times 10^{11}$ particles/ml) were purchased from Ted Pella, Inc. The matched pair of monoclonal antibodies utilized for the sandwich assay was obtained from research Diagnostics. The pair consisted of mouse anti-human free PSA clone PSA-F65, which was used as the capture antibody after immobilization on gold-coated glass chips, and mouse anti-human PSA clone PSA-66, which was employed as the tracer antibody after conjugation to the gold particles as described below.

Serum PSA (10-30% free PSA) was purchased from Bios Pacific, and buffer packs and ImmunoPure normal human serum were acquired from Pierce Biotechnology. N-hydrosysuccinimide (NHS), 1,3-dicyclohexylcarbodiimide (DCCD), Tween 80, 5,5'-dithiobis(2-nitrobenzoid acid) (DNBA), and bovine serum albumin (BSA) were obtained from Aldrich. Applicants note that unless otherwise specified, all reagents were used as received or were reconstituted according to standard methodologies. The preparation of dithiobis (succinimide undecanoate) (DSU) followed a modification to recent literature procedures; (Wagner et al., *Biophys. J.* 1996, 70,2052-66.)

Example 9

Synthesis of 5,5'-Dithiobis(succinimidyl-2-nitrobenzoate) (DSNB)

The Raman-active reporter molecule 5,5'-Dithiobis(succinimidyl-2-nitrobenzoate) (DSNB) was synthesized following a procedure similar to that described herein above and in Porter et al., *Anal. Chem.;* 2003, 1;75(21):5936-43 (incorporated by reference herein in its entirety). Briefly, to 50 mL of dry tetrahydrofuran was added 0.50 g of DNBA (1.3 mmol), 0.52 g of DCCD (2.5 mmol), and 0.29 G of NHS (2.5 mmol) in a 100-mL round-bottom flask equipped with a drying tube. The mixture was magnetically stirred at 25° C. for 12 h, filtered, and then rotoevaporated to remove solvent. The crude product was recrystallized from acetone/hexane, yielding a yellow powder: 1H NMR (CDCl$_3$) δ=8.13 (d, 2H, $^3$JH, H=8 Hz, C$_6$H$_4$), 7.85 (d, 2H, $^3$JH,H=8 Hz, C$_6$H$_4$), 7.97 (s, 2H, C$_6$H$_4$), 2.91 (s, 8H, CH$_2$).

Example 10

Preparation of Raman Reporter-Labeled Immunogold Colloids

Figure 8:
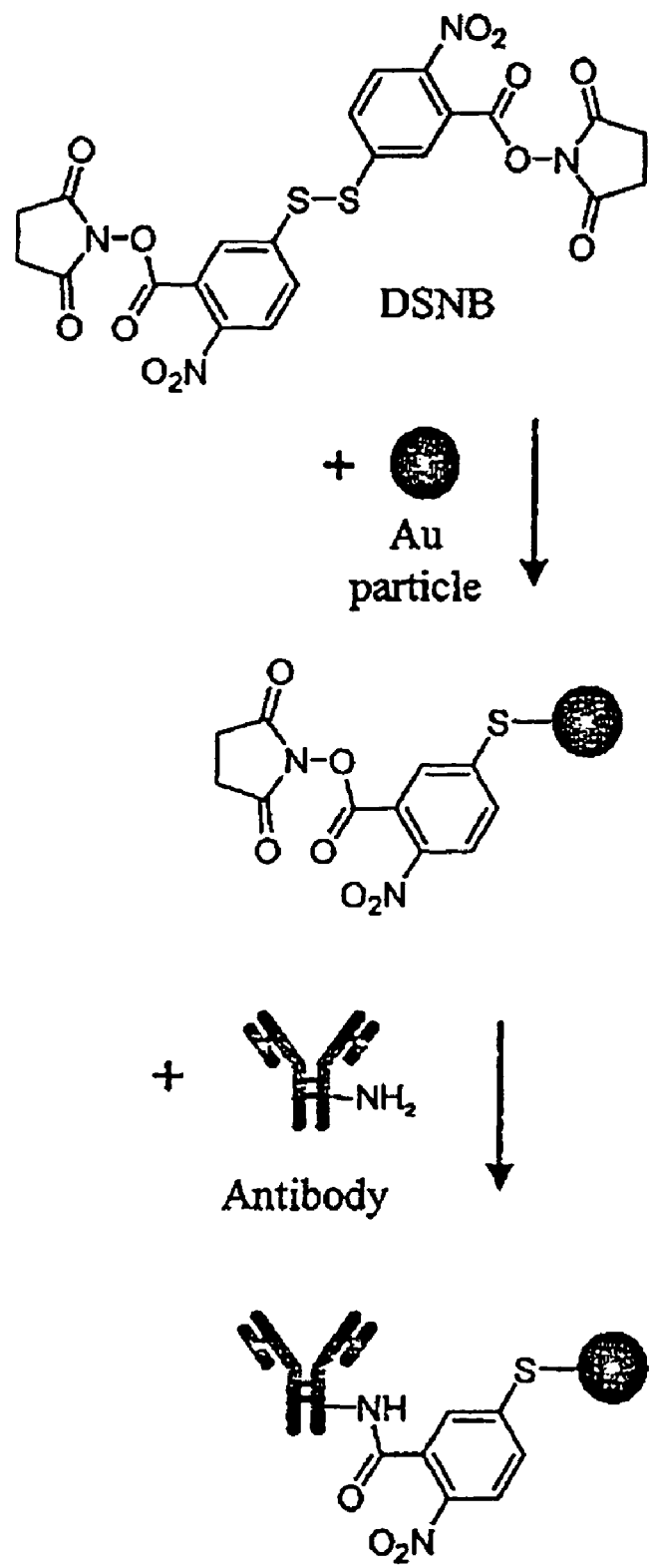
FIG. 8 is schematic illustrating the process for preparing a Raman reporter-labeled immunogold colloid.

Raman Reporter-labeled immunogold colloids were prepared using various derivatives of dithiobis (benzoic acid), which could easily be converted to the corresponding succinimide ester with NHS. Of those tested, DSNB is a particularly attractive example because of the strong scattering cross section of its symmetric NO$_2$ stretch. As such, treatment of colloidal gold with this derivative (FIG. 8) yields a coating of the thiolate of DSNB, which can couple to the primary amines of a tracer antibody by formation of an amide linkage. Applicants note that this design strategy minimizes the distance between the gold surface and label scattering center. This minimization is particularly significant because, according to a simplified electromagnetic model, enhancement varies inversely with the 12th power of the separation distance between the scatterer and the metal particle center.

The particle workup consisted of two steps. In step one, 100 µL of a 2.5 mM DSNB solution in acetonitrile was added to 1 mL of the unconjugated colloidal gold suspension and the mixture reacted for 3-5 h. The reporter-labeled colloids were then separated from solution by centrifugation at 10000 g for 7 min. The clear supernatant was discarded, and the loose red sediment was resuspended in 1 mL of borate buffer (2 mM, pH 9).

In step two, mouse anti-PSA was coupled to the gold particles via the succinimidyl terminus of the DSNB-derived coating. As such, 35 µg of detection antibody (7 µL of 5 mg/mL PSA-66 solution) was added to the 1-mL suspension of the reporter-labeled colloid. The mixture was then incubated at room temperature for 1 h. After centrifugation at 10000 g for 7 min and removal of the supernatant, the red sediment was resuspended in 1 mL of 2 mM Tris buffer (Tris-HCl (pH 7.6), 1% BSA). Appliants note that the use of BSA, Tween 80, or both in all of the preparative steps and in the assay protocol is part of a general procedure designed to minimize complications from nonspecific adsorption.

Example 11

Preparation of Capture Antibody Substrates

Capture antibody substrates were prepared by first cleaning glass slides in an ultrasonic bath under dilute surfactant solution (Micro, Cole-Parmer), deionized water, and methanol, each for 30 min. The slides were then loaded into an Edwards 306A metal evaporator and coated with 15 nm of chromium and 300 nm of gold at 0.2 nm/s at pressures less than 5×10−6 Torr. Next, the gold substrates were removed from the evaporator and exposed for ~30 s to an octadecanethiol (ODT)-soaked poly(dimethylsiloxane) stamp, which had a 5-mm-diameter hole cut in its center. This step "inks" the outer portion of the gold substrate with a monolayer of ODT. After inking, the substrates were rinsed with ethanol, dried under a stream of nitrogen, and immersed in a 1 mM ethanolic solution of DSU for 6-12 h. Upon removal from solution, the substrates were rinsed again with ethanol and dried under a stream of nitrogen. The result is a 5-mm-diameter domain of the succinimide ester-terminated monolayer on each substrate, surrounded by a hydrophobic ODT coating. Applicants note that the ODT coating serves as a hydrophobic barrier that localizes aqueous protein solutions when pipetted onto the area of the substrate defined by the DSU-derived monolayer.

Anti-free PSA antibodies (PSA-65) were immobilized by pipetting 40 µL of the protein solution (100 µg/mL in 0.05 M borate buffer (pH 9) and 1% Tween 80) onto the localized domain of the DSU-modified monolayer. The reaction was allowed to progress overnight at room temperature. After rinsing three times with buffer 1 (0.01 M borate buffer (pH 9), 30 mM NaCl, 0.5% Tween 80), 40 µL of blocking buffer (5% BSA in 0.05 M borate buffer (pH 9) was pipetted onto the surface and incubated for 1 h. The substrates were then rinsed three times with buffer 1.

Example 12

Immonoassay Protocol

PSA dose-response curves were constructed using matrixes consisting of normal human serum, 10 mM phosphate-buffered saline (PBS, KH2PO4/K2HPO4 (pH 7.5), 150 mM NaCl, 0.1% BSA, 0.5% Tween 80, 0.02% NaN3), and a 1:1 mixture of human serum and PBS, following the typical procedure for a sandwich-type assay. For each matrix, 40 µL aliquots of PSA solutions of various concentrations were pipetted onto a capture antibody-coated substrate and allowed to react for 3 h at room temperature. After rinsing three times with buffer 2 (10 mM PBS buffer (pH 7.5), 0.5% Tween 80, 0.02% NaN3), the sample was exposed to 40 µL of the immunogold detection reagent for 6 h. All samples were then rinsed three times with buffer 2 and once with deionized water and dried under a stream of nitrogen before SERS characterization. Applicants found that Tween concentrations of 0.1-0.5% in the rinse buffer were generally effective in minimizing nonspecifically bound protein, while maintaining the hydrophobic integrity of the ODT domain.

Example 13

Instrumentation (i) SERS Measurements.

Figure 9:
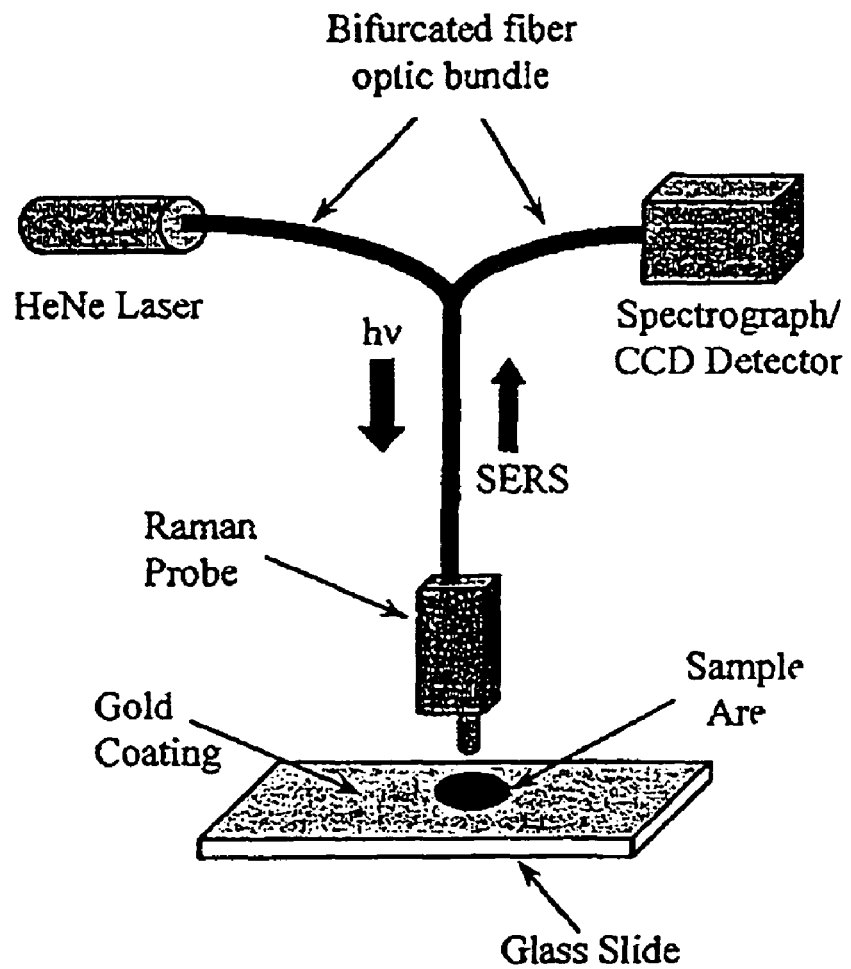
FIG. 9 illustrates the experimental setup for measuring PSA levels in human serum using surface-enhanced Raman spectroscopy.

A fiber-optic based Raman system, NanoRamon I, from NanoRaman Instruments was used for all Raman data generation. The system consists of three major subassemblies: laser light source, spectrograph, and fiber-optic probe. FIG. 9 shows the spectroscopic setup The light source is a 30-mW, 632.8-nm HeNe laser, while the spectrograph consists of an f/2.0 Czerny-Turner imaging spectrometer (6-8-cm$^{-1}$ resolution, no moving parts) and a thermoelectrically cooled (0° C.) Kodak 0401E CCD. The fiber-optic probe (1.75×2.5×6 in) utilizes band-pass and long-pass filters for laser light (OD 6) and fiber background (OD 4) rejection. The probe objective provides a numerical aperture of 0.65 while maintaining a relatively long working distance of 3 mm. The laser spot size on the sample surface is ~22 µm in diameter. A Windows-based Visual Basic program controls the system. All spectra were collected with a 60-s integration time. The positions of the Raman bands were determined by comparisons to the known positions of bands for solid naphthalene.

(ii) Infrared Spectroscopy.

Infrared reflection spectra were acquired with a Nicolet 850 FT-IR spectrometer, purged with liquid $N_2$ boil-off, and equipped with a liquid $N_2$-cooled HgCdTe detector. Spectra were obtained using p-polarized light incident at 80° with respect to the surface normal. The spectra were recorded as—log(R/Ro), where R is the sample reflectance and Ro is the reflectance of an octadecanethiolate-$d_{37}$ monolayer-coated Au reference. The spectra are an average of 512 sample and reference scans, taken at 4 $cm^{-1}$ resolution with Happ-Genzel apodization.

(iii) X-ray Photoelectron Spectroscopy.

X-ray photoelectron spectra (XPS) were acquired at room temperate with a Physical Electronics Industries 5500 multi-technique surface analysis system. This system is equipped with a hemispherical analyzer, a toroidal monochromator, a multichannel detector at 45°, and monochromatic Al Kα excitation radiation (1486.6 eV, 250 W). A pass energy of 29.35 eV was used, giving a half-width of the Au($4f_{7/2}$) peak of ~0.8 eV.

Results and Discussion

Chip Characterization

The capture antibody substrate consisted of anti-free PSA bound to a gold-coated glass chip via the DSU-derived coupling agent. DSU chemisorbs to gold through cleavage of the sulfur-sulfur bond, and the formation of the resulting gold-bond thiolate and its subsequent coupling to anti-free PSA can be readily confirmed by infrared reflection spectroscopy (IRS) and XPS. The IRS results are presented in FIG. 10. The three bands around 1800 $cm^{-1}$ in the spectrum of the layer formed from DSU (FIG. 10A) are assigned to the carbonyl stretches of the ester (1816 $cm^{-1}$) and of the succinimidyl end group (1787 (in-phase) and 1750 $cm^{-1}$ (out-of-phase)). The presence of these bands, along with the succinimidyl bands at 1219 and 1078 $cm^{-1}$ and the methylene stretches between 3000 and 2800 $cm^{-1}$, verifies the formation of the DSU-based coating.

Figure 10:
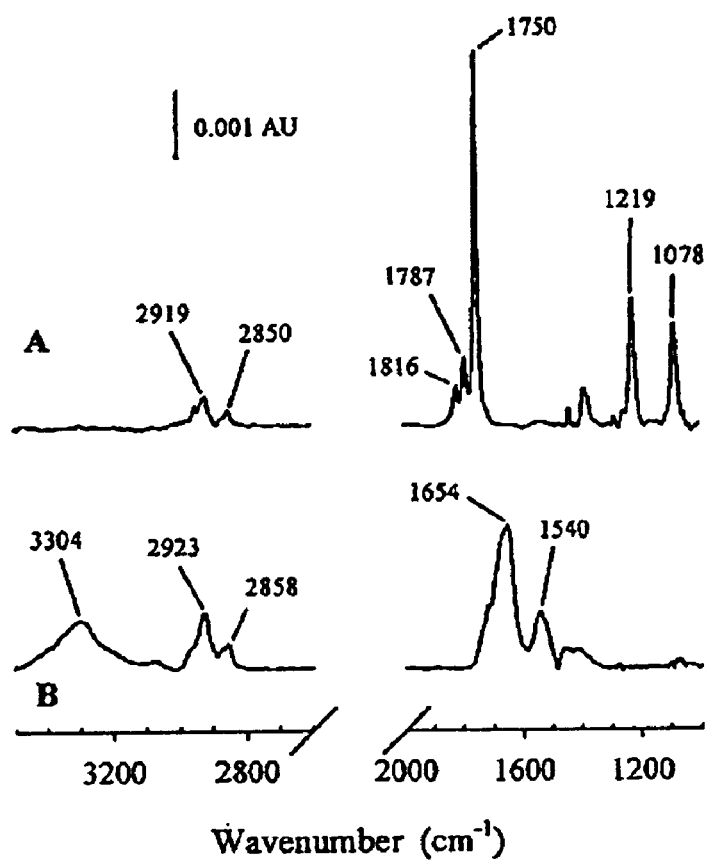
FIG. 10 shows an infrared reflection spectra of DSU-derived monolayer on gold before (spectrum A) and after (spectrum B) exposure to the anti-free PSA capture antibody.

IRS was also used to confirm the covalent binding of anti-free PSA to the terminal group of the gold-bound coupling layer (FIG. 10B). Since the acyl carbon of the succinimidyl ester group is strongly susceptible to nucleophilic attack, reaction with the sterically accessible amines in the protein should immobilize anti-free PSA via amide linkages. As evident in FIG. 2B, treatment of the DSU-modified substrate with anti-free PSA causes a marked decrease in the magnitude of the bands for the succinimidyl group (e.g., 1750, 1219, and 1078 $cm^{-1}$). Moreover, three readily identifiable bands, which are located at 3304 (N—H stretch), 1654 (amide I), and 1540 $cm^{-1}$ (amide II), have appeared. The new bands reflect the presence of amides inherent in the native antibody as well as those formed by the reaction of the succinimidyl groups of DSU with amines in the protein. Coupled with earlier reports, which, in part studied the hydrolysis rate of the succinimidyl terminal group of DSU-derived monolayer under similar conditions, the differences in FIG. 10 support the covalent attachment of anti-free PSA to the underlying substrate.

The XPS characterizations are in agreement with the IRS findings. The results for both modified surfaces are given in Table 1 shown below.

TABLE 1

Binding Energies (eV) and Compositional Assignments for XPS Spectra of DSU and DSNB Monolayers on Gold before and after Antibody Derivitization

| Core level | DSU/Au | Anti-free PSA/DSU/Au | DSNB/Au | Anti-PSA/ DSNB/Au |
|---|---|---|---|---|
| Au($4f_{7/2}$) | 83.9 | 83.9 | 83.9 | 83.9 |
| S($2p_{3/2}$) | 161.8 | 161.8 | 162.2 | 162.2 |
| S($2p_{1/2}$) | 162.9 | 162.9 | nd[a] | nd |
| C(1s) | 289.0 | 288.5 | 288.4 | 288.1 |
| C(1s) | 284.4 | 284.9, 286.4 (sh) | 284.6 | 284.8,285.9(sh) |
| N(1s) | 401.9 | 400.5 | 405.6, 401.2 | 405.2,400.0 |
| O(1s) | 532.5, 534.9 | 432.1 | 532.2 | 532.2 |

[a]nd, not detected.

As expected, survey spectra for the two different coatings showed only the presence of carbon, oxygen, nitrogen, and sulfur. For the DSU-based coating, the C (1s) region was composed of a lower energy band (284.4 eV), attributed to the alkyl chain structure of the coating, and a higher energy band (289.0 eV), assigned to the different types of carbonyl carbon. Two bands were also observed in the O(1s) and S(2p) regions. In the O(1s) region, the band at 534.9 eV is ascribed to the oxygen of the ester linkage and that at 532.5 eV is assigned to the remaining carbonyl oxygens. In the S(2p) region, the positions of the features in the doublet that arises from spin-orbit coupling ($2p_{3/2}$, 161.8 eV; $2p_{1/2}$, 162.9 eV) are consistent with the presence of gold-bound thiolates formed by the adsorption of thiols and disulfides on gold. In contrast, there was only one band observed in the N(1s) region. The location of this band (401.9 eV) agrees with the presence of an electron-withdrawing group attached to nitrogen, as is the case for the succinimidyl nitrogen.

After treatment with anti-free PSA, all XPS features undergo a general broadening, which limited the ability to carry out an in-depth compositional analysis. There were, however, two readily identifiable changes that support the coupling of anti-free PSA to the DSU-derived coating. First the N(1s) band shifts from 401.9 to 400.5 eV. This shift is ascribed to the loss of the succinimidyl end group and the appearance of the numerous nitrogen functionalities in the immobilized protein. Second, the intensity of the S(2p) couplet is greatly diminished. The decrease in intensity reflects the attenuation of the photoelectrons by the immobilized protein.

Detection Reagent Characterization

Figure 11:
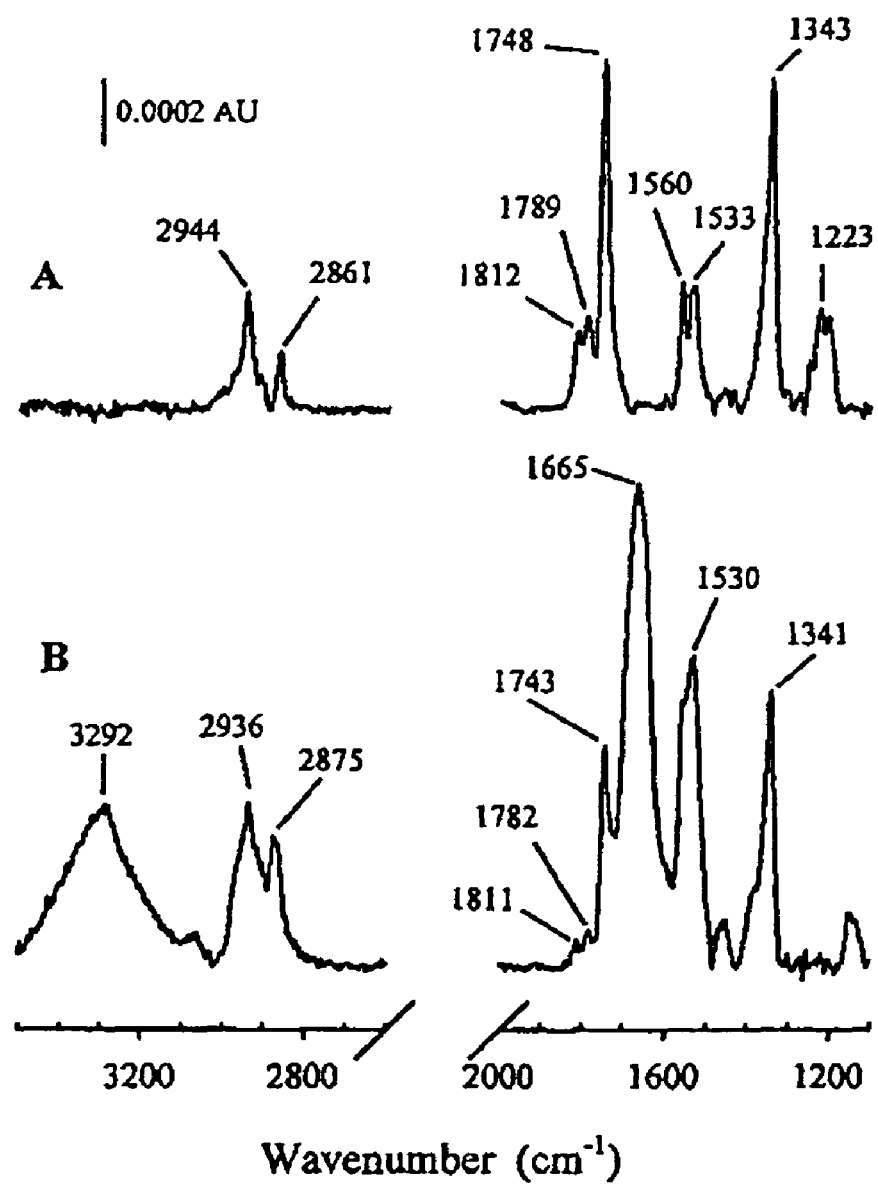
FIG. 11 shows an infrared reflection spectra of a DSNB-derived monolayer on gold before (spectrum A) and after (spectrum B) exposure in the anti-PSA tracer antibody.

The new Ramen reporter molecules, which were prepared by reacting DNBA with NHS to form the bis(succinimide ester), yield a coating on gold that can act as a coupling agent in the same manner as the DSU-based monolayer. FIG. 11 shows the IRS spectra for a monolayer of DSNB spontaneously adsorbed on gold-coated glass before and after exposure to anti-PSA. The as-formed layer has carbonyl stretches at 1812, 1789, and 1748 $cm^{-1}$ and strong symmetric and asymmetric nitro stretches at 1343 and 1533 cm$^{-1}$, respectively. As with the DSU-based monolayer, the spectrum for the DSNB-derived monolayer undergoes a similar set of changes following exposure to anti-PSA. Three new bands appear (3292 (N—H stretch), 1655 (amide I), and 1530 cm$^{-1}$ (amide II)), and the three carbonyl stretches exhibit a notable decrease. The detection of residual succinimide groups is expected because the presence of an immobilized antibody will sterically hinder protein binding to neighboring succinimide moieties. Thus, BSA was used in the immunogold reagent preparation procedure to react with any exposed residual succinimide groups in order to preclude their participation in nonspecific binding.

The XPS characterizations (Table 1) also strongly mimic those for the DSU-based layer. In this case, however, there are two N(1s) bands for each sample. For the as-formed layer, bands at 401.2 and 405.5 eV are indicative of the succinimidyl nitrogen and nitro nitrogen on the aromatic ring, respectively. After exposure to anti-PSA, the band at 401.2 eV disappears and one at 400.0 eV appears. This change again parallels that for the DSU-derived coating.

SERS of Reporter-Labeled Immunogold Reagent

Figure 12:
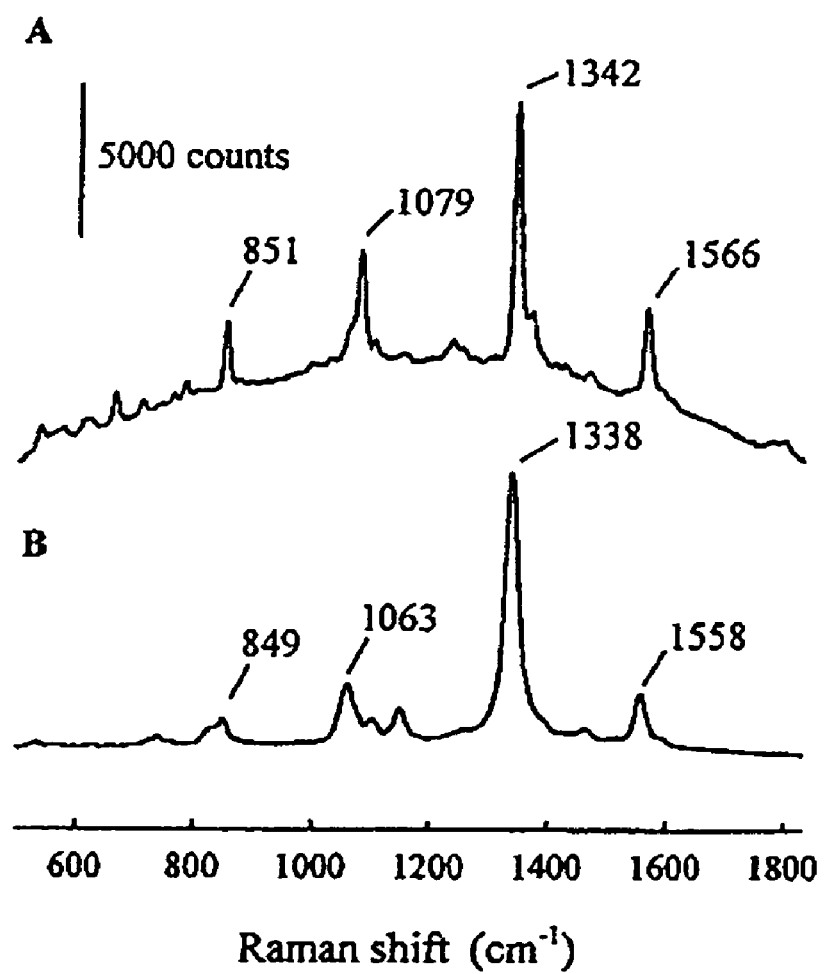
FIG. 12 shows a Raman spectra of the reporter compound: (A) spectrum of DSNB powder; (B) SERS spectrum of gold nanoparticles following reaction with DSNB.

Raman spectra for the Ramen reporter molecule DSNB are shown in FIG. 12 before and after coupling to the gold nanoparticles. The nanoparticle sample was prepared by drop casting a small amount of the labeled colloid solution onto a gold-coated glass slide and evaporating the water-based solvent. The powder spectrum (FIG. 12A) is dominated by the symmetric nitro stretch at 1342 cm$^{-1}$, and we attribute the band at 851 cm$^{-1}$ to the nitro scissoring vibration. The band at 1566 cm$^{-1}$ is assigned to an aromatic ring mode (8a), and the large band at 1079 cm$^{-1}$ is probably a succinimidyl N—C—O stretch overlapping with aromatic ring modes.

Many of the bands in the powder spectrum are present in the spectrum after DSNB is chemisorbed onto the gold nanoparticles (FIG. 12B), though some have undergone a small change in position. For example, the symmetric nitro stretch has shifted from 1342 to 1338 cm$^{-1}$, and the 8a mode has moved from 1566 to 1558 cm$^{-1}$. These shifts are indicative of interactions between neighboring adsorbates and between the adsorbates and the gold surface. Additionally, since there was no detectable Raman signal for the monolayer formed from DSNB adsorbed to a smooth gold surface, the spectrum in FIG. 12B illustrates that the immobilization of DSNB on the gold nanoparticles results in a significant level of enhancement, the magnitude of which will be examined in detail in future studies. Together, these results confirm that the particles have been effectively modified with the DSNB-based RRMs.

SERS Immonoassay Detection of Free PSA

Figure 13:
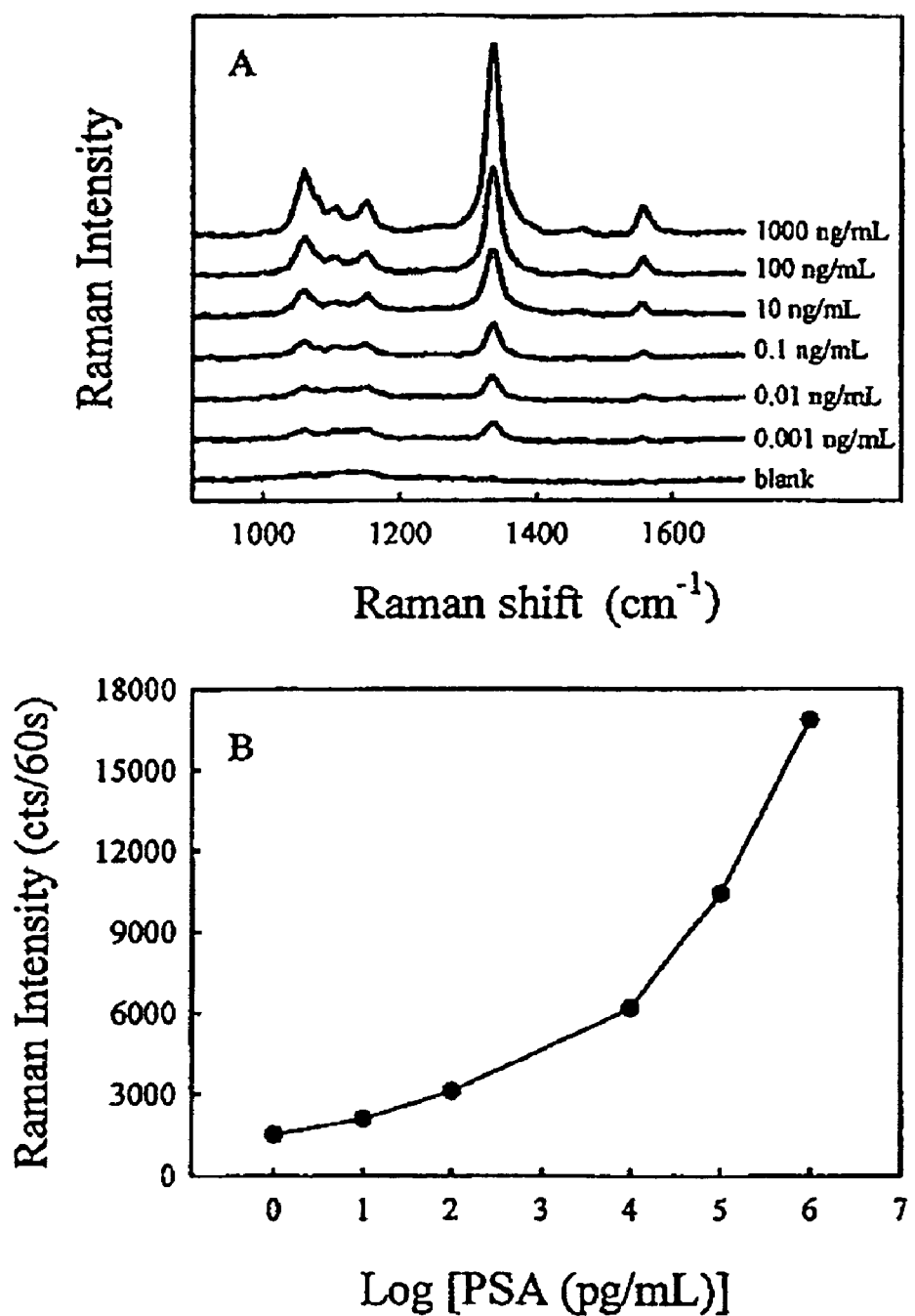
FIG. 13 illustrates a SERS-based free PSA immunoassay: (A) SERS spectra, offset for clarify, acquired at various PSA concentrations; (B) dose-response curve for free PSA in human serum. The dose-response curve was constructed by calculating the average reading of the response for 6-8 different locations on the surface of each sample, which typically varied by 10% as described in the detailed description below.

The results of our SERS-based determinations for free PSA in normal human serum are shown in FIG. 13. Test solutions were made by serial dilution in human serum of a 1 mg/mL PSA standard to cover the range from 1 µg/mL (30 nM) to pg/mL (30 fM). The spectra in FIG. 13A were obtained using 60-s integrations after completion of the immunoassay protocol outlined above. As is evident, the features diagnostic of the DSNB-labeled nanoparticles exhibit a strong increase as the PSA level increases. These changes span more than 6 order of magnitude, this encompassing concentration levels critical to prostate cancer diagnosis.

The lower limit of detection by the nonspecific adsorption of the labeled nanoparticles, as demonstrated by the signal observed for the blank serum sample. Blanks prepared without BSA and Tween 80 as additives yielded signals that were several times larger than those obtained with the use of additives. In contrast, the packing constraints imposed by the labeled particle size should control the upper limit of the dynamic range. Though only examined in a preliminary manner, tests place the upper limit at ~10 µg/mL.

A more detailed treatment of applicants' findings is presented by the dose-response curve in FIG. 13B. This curve was constructed by plotting the scattering intensity of the symmetric nitro stretch (1338 cm$^{-1}$, full width at half-maximum of 22 cm$^{-1}$). Each data point represents the average of six to eight readings across the sample surface. Variations in signal strength across the surface of each chip were typically ~10%. However, signal strengths up to twice as large as those represented in the plot were observed ~20% of the time. The does-response curve was constructed by omitting the data for these "hot spots". These hot spots could possibly reflect the presence of domains where there are higher localized concentrations of binding sites and, therefore, higher particle densities are reasonably homogenous over areas irradiating by the laser source. On the other hand, AFM imaging revealed a small number of particle aggregates that could account for the hot spots. A third possibility arises from the existence of "hot particles". Recent studies have shown that enhancement factors are strongly dependent on particle size, shape, and excitation wavelength and that a small fraction of particles exhibit markedly larger enhancements.

The dose-response curve shows that our detection platform can determine free PSA at very low concentrations in human serum. The detection limit is ~1 pg/mL. These results compare favorably with commercial assays based on radiometric, chemiluminescent, and ELISA methods, which have detection limits ranging from 3 to 1000 pg/mL free PSA. Additional studies were performed in which PSA was added to 10 mM PBS that contained 0.1% BSA and 0.5% Tween 80. These studies yielded a detection limit of 4 pg/mL free PSA, based on a concentration that produces a signal three times the standard deviation of the background. Similar results were obtained in a analyte matrix of a 1:1 mixture of PBS/serum. Thus, the assay appears to be applicable to a range of sample matrixes.

The ability to detect exceedingly small amounts of analyte using our monoclonal-based assay format is underscored by a rough estimate of the number of molecular recognition events responsible for the response at the limit of detection. At a detection limit of 4 pg/mL, a 40 µL solution of free PSA contains 160 fg (~3×106 molecules) of free PSA. If we assume that (1) the capture surface exhaustively binds all of the proteins, (2) the captured antigens are uniformly distributed across the 5-mm-diameter surface of the capture substrate, and (3) the binding stoichiometry between the nanoparticles and captured antigen is 1:1, then there are only ~60 PSA molecules in the 22 µm-diameter area irradiated by the laser source. This analysis shows that the combination of surface enhancement with respect to the close proximity of the scattering site to the particle surface, the amplification due to the large number of Ramen reporter molecules coating each particle (preliminary estimates indicate that there are ~10$^3$ RRMs tethered to each nanoparticle), and the binding affinity of monoclonal antibodies leads to an extremely low level of detection.

Based on the estimate of the number of recognition events detected in the above-described PSA assay, projections can be made which strongly argue that the technique can be extended to single-molecule detection. There are two clear avenues to reach such a level. The first avenue uses labels that undergo both resonance and surface enhancement. With resonance enhancement, intensities can be 2-6 orders of magnitude greater than those based on normal Raman scattering. The second avenue takes advantage of recent reports that have shown that the surface enhancement for slightly larger gold particles (e.g., 60 nm for our excitation wavelength) is greater than that for 30-nm particles. Taken together, the ability to detect the binding of a single antigen appears to be well within reach and should be of immense value in the ultra-low-level detection of a wide range of biomarkers used in early disease diagnosis and other assay applications. Low-level detection becomes even more important as the degree of multiplexing increases, e.g., in instances where screening for multiple analytes at a single location is of interest.

Therefore, this embodiment of the present invention enables the detection of biomarkers for early cancer diagnosis in serum samples at very low concentrations by a SERS-based readout method. This strategy is capable of encompassing a wide range of applications, especially in view of the opportunities to multiplex through the judicious design of more labeled nanoparticles. As such, multiple analytes could be concurrently identified through the position of a characteristic feature of the Raman label and then quantified by its intensity.

It is envisioned that assays could be developed for the high-sensitivity, simultaneous screening of a battery of cancer markers using a single serum sample, saving time, reducing assay costs, and potentially leading to earlier diagnosis.

Although the foregoing invention has been described in some detail by way of illustration and example for purposes of clarity of understanding, it will be readily apparent to those of ordinary skill in the art in light of the teachings of this invention that certain changes and modifications to the disclosed reagents, methods and kits may be made thereto without departing from the spirit or scope of the appended claims.

We claim:

1. A Raman-active reagent comprising a non polymeric bi-functional Raman-active reporter molecule monolayer which includes a reactive group, a binding molecule, and a surface enhancing particle capable of causing surface enhanced Raman scattering, the Raman-active bi-functional monolayer reporter molecule being chemically linked to the surface enhancing particle and providing a detectable or measurable Raman scattering signal when illuminated by an excitation source capable of inducing a Raman scattering, the Raman-active reporter molecule operably linked to the binding molecule through the reactive group, wherein the binding molecule is capable of specifically binding to a target analyte, and wherein the Raman-active reporter molecule operably links the binding molecule to the surface enhancing particle to form a Raman-active reagent.

2. The Raman-active reagent of claim 1 wherein the binding molecule is selected from the group of lectins, lectin fragments, lectin derivatives, antigens, monoclonal antibodies, polyclonal antibodies, immunoreactive fragments, immunoreactive derivatives, peptides, haptens, aptamers, nucleic acid molecules, crown ethers, cyclodextrins, cryptands, and calixarenes.

3. The Raman-active reagent of claim 1 wherein the binding molecule is anti-prostate-specific antigen (anti-PSA).

4. The Raman-active reagent of claim 1 wherein the Raman-active reporter molecule is selected from the group consisting of dithiobisbenzonic acid, 4-mercaptobenzoic acid, 4,4'-dithiobis(succinimidylbenzoate), direct red 81, Chicago sky blue, p-dimethylaminoazobenzene, 4-(4-Aminophenylazo)phenylarsonic acid monosodium salt, 1,5-difluoro-2,4-dinitrobenzene, arsenazo I, basic fuchsin, disperse orange 3, HABA (2-(4-hydroxyphenylazo)-benzoic acid, erythrosine B, trypan blue, ponceau S, ponceau SS, 5,5'-dithiobis(2-nitrobenzoic acid), metal complexes and polymeric particles.

5. The Raman-active reagent of claim 1 wherein the reactive group is a terminal functional group of a reactive compound that is selected from the group consisting of succinimides, maleimides, isothiocyanates, isocyanates, acyl azides, sulfonyl chlorides, aldehydes, glyoxals, epoxides, oxiranes carbodiimides, carbonates, arylating agents, acryloyl derivatives, diazoalkanes, diazoacetyl compounds, anhydrides, aziridines, imidoesters, or carbonyldiimidazole.

6. The Raman-active reagent of claim 1 wherein the reactive group is a terminal succinimide group of the reactive compound N-hydroxysuccinimide (NHS).

7. The Raman-active reagent of claim 1 wherein the surface enhancing particle comprises a metallic material.

8. The Raman-active reagent of claim 7 wherein the metallic material is either gold, silver, copper, platinum, aluminum, gallium, indium, zinc or cadmium.

9. The Raman-active reagent of claim 8 wherein the metallic material is gold.

10. The Raman-active reagent of claim 1 wherein the surface enhancing particle is either a silica, plastic, glass, carbon, ceramic or magnetic material, coated with a metallic material.

11. A Raman-active reagent comprising a Raman-active reporter molecule which includes a reactive group, a binding molecule, and a surface enhancing particle being a colloidal gold particle capable of causing surface enhanced Raman scattering, the Raman-active reporter molecule being 5,5'-disthiobis(succinimidyl-2-nitrobenzoate) linked to the surface enhancing particle by a thiol linkage and providing a detectable or measurable Raman scattering signal when illuminated by an excitation source capable of inducing a Raman scattering, the reactive group being the succinimide of the disthiobis(succinimidyl-2-nitrobenzoate), and wherein binding molecule is an antibody capable of specifically binding to a target analyte.

12. A kit for determining the presence or amount of a target analyte in a test sample, the kit comprising:
 (a) a Raman-active reagent including a bi-functional non polymeric Raman-active reporter molecule monolayer which includes a reactive group, a binding molecule, and a surface enhancing particle capable of causing surface enhanced Raman scattering, the Raman-active reporter molecule being chemically linked to the surface enhancing particle and providing a detectable or measurable Raman scattering signal when illuminated by an excitation source capable of inducing a Raman scattering, the Raman-active reporter molecule operably linked to the binding molecule through the reactive group, and wherein the Raman-active reporter molecule operably links the binding molecule, capable of specifically binding a target analyte, to the surface enhancing particle to form a reagent/analyte complex; and
 (b) a substrate capable of binding the target analyte or the reagent/analyte complex prior to inducing Raman scattering with the excitation source.

13. The kit of claim 12 wherein the binding molecule is selected from the group of lectins, lectin fragments, lectin derivatives, antigens, monoclonal antibodies, polyclonal antibodies, immunoreactive fragments, immunoreactive derivatives, peptides, haptens, aptamers, nuclei(original) c acid molecules, crown ethers, cyclodextrins, cryptands, and calixarenes.

14. The kit of claim 12 wherein the binding molecule is anti-prostate-specific antigen (anti-PSA).

15. The kit of claim 12 wherein the Raman-active reporter molecule is selected from the group consisting of dithiobisbenzonic acid, 4-mercaptobenzoic acid, 4,4'-dithiobis(succinimidylbenzoate), direct red 81, Chicago sky blue, p-dimethylaminoazobenzene, 4-(4-Aminophenylazo) phenylarsonic acid monosodium salt, 1,5-difluoro-2,4-dinitrobenzene, arsenazo I, basic fuchsin, disperse orange 3, HABA (2-(4-hydroxyphenylazo)-benzoic acid, erythrosine B, trypan blue, ponceau S, ponceau SS, 5,5'-dithiobis(2-nitrobenzoic acid), metal complexes and polymeric particles.

16. The kit of claim 12 wherein the reactive group is terminal functional group of a reactive compound that is selected from the group consisting of succinimides, maleimides, isothiocyanates, isocyanates, acyl azides, sulfonyl chlorides, aldehydes, glyoxals, epoxides, oxiranes carbodiimides, carbonates, arylating agents, acryloyl derivatives, diazoalkanes, diazoacetyl compounds, anhydrides, aziridines, imidoesters, or carbonyldiimidazole.

17. The kit of claim 12 wherein the reactive group is a terminal succinimide group of the reactive compound N-hydroxysuccinimide (NHS).

18. The kit of claim 12 wherein the surface enhancing particle comprises a metallic material.

19. The kit of claim 18 wherein the metallic material is either gold, silver, copper, platinum, aluminum, gallium, indium, zinc or cadmium.

20. The kit of claim 19 wherein the metallic material is gold.

21. The kit of claim 12 wherein the surface enhancing particle is either a silica, plastic, glass, carbon, ceramic or magnetic material, coated with a metallic material.

22. The kit of claim 21 wherein the metallic material is either gold, silver, copper, platinum, aluminum, gallium, indium, zinc or cadmium.

23. The kit of claim 22 wherein the metallic material is gold.

* * * * *